United States Patent
Banks et al.

(10) Patent No.: US 10,487,339 B2
(45) Date of Patent: *Nov. 26, 2019

(54) TRANSGENIC SOYBEAN PLANTS AND CHROMOSOMES

(71) Applicant: Monsanto Technology, LLC, St. Louis, MO (US)

(72) Inventors: Isaac Richard Banks, Kirkwood, MO (US); Sergey Ivashuta, Ballwin, MO (US); Barbara Elizabeth Wiggins, Chesterfield, MO (US); Yuanji Zhang, Weldon Spring, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,546

(22) Filed: Nov. 29, 2017

(65) Prior Publication Data

US 2018/0171350 A1 Jun. 21, 2018

Related U.S. Application Data

(63) Continuation of application No. 13/502,737, filed as application No. PCT/US2009/068754 on Dec. 18, 2009, now Pat. No. 9,873,888.

(60) Provisional application No. 61/254,555, filed on Oct. 23, 2009.

(51) Int. Cl.
*C12N 15/82* (2006.01)

(52) U.S. Cl.
CPC ..... *C12N 15/8262* (2013.01); *C12N 15/8218* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,731,179 A | 3/1998 | Komari et al. |
| 5,824,877 A | 10/1998 | Hinchee et al. |
| 7,002,058 B2 | 2/2006 | Martinell et al. |
| 7,288,694 B2 | 10/2007 | Armstrong et al. |
| 8,030,544 B2 | 10/2011 | Martinell et al. |
| 8,062,885 B2 | 11/2011 | Mach et al. |
| 2005/0183170 A1 | 8/2005 | Fillatti et al. |
| 2008/0256669 A1 | 10/2008 | Fabbri et al. |
| 2009/0151021 A1* | 6/2009 | Bots ............... C12N 15/8218 800/287 |
| 2009/0156793 A1 | 6/2009 | Gilbertson et al. |
| 2011/0296555 A1 | 12/2011 | Ivashuta et al. |

FOREIGN PATENT DOCUMENTS

| | | |
|---|---|---|
| WO | WO 2008/133643 | 11/2008 |
| WO | WO 2010/002984 | 1/2010 |

OTHER PUBLICATIONS

Franco-Zorrilla et al, 2007, Nature Genetics, 39:1033-1037.*
PCT, Notification of Transmittal of the International Search Report and Written Opinion of the International Searching Authority (ISA/US) for PCT/US09/68754, dated May 10, 2010.
Reinhart et al., "MicroRNAs in Plants," *Genes Deb.*, 16:1616-1626, 2002.
Zhang et al., "Identification of Soybean microRNAs and their Targets," *Planta*, 29:161-182, 2008.
Ivashuta et al., "Regulation of Gene Expression in Plants through miRNA Inactivation," *PLoS one*, www.plosone.org, 6(6), e21330. doi:10. 1371, Jun. 2011.
Banks et al., "RNA decoys: Am emerging component of plant regulatory networks?," *Plant Signaling & Behavior*, 7(9):1188-1193, 2012.
Franco-Corrilla et al., "*Nature Genetics*", 39:1033-1037, 2007.

* cited by examiner

*Primary Examiner* — Jason Deveau Rosen
(74) *Attorney, Agent, or Firm* — Dentons US LLP; David Lanzotti

(57) ABSTRACT

Described herein are transgenic soybean chromosomes containing a recombinant DNA that transcribes to an RNA molecule that hybridizes to and forms a cleavage-resistant duplex with either a mature miR171 miRNA or a transcript of a target gene having a recognition site for a mature miR171 miRNA whereby the function of the miR171 miRNA is inhibited and thereby imparts enhanced agronomic traits to soybean plants such as increased pods per node, increased number of nodes, a decreased distance between nodes, and a twisted stem.

21 Claims, 4 Drawing Sheets

Specification includes a Sequence Listing.

4A

4B

TRANSGENIC SOYBEAN PLANTS AND CHROMOSOMES

CROSS REFERENCE TO RELATED APPLICATIONS

This application is a continuation of co-pending U.S. patent application Ser. No. 13/502,737, filed Jul. 2, 2012, which is a 371 National Stage Application of PCT/US2009/68754, filed Dec. 18, 2009, which claims the priority of U.S. Provisional Application Ser. No. 61/254,555, filed Oct. 23, 2009, which are herein incorporated by reference in its entirety.

INCORPORATION OF SEQUENCE LISTINGS

The sequence listing that is contained in the file named "38-21-56969BPCT.txt", which is 26.3 kilobytes as measured in Microsoft Windows operating system and was created on 11 Dec. 2009, is filed electronically herewith and incorporated herein by reference.

FIELD OF THE INVENTION

Disclosed herein are transgenic chromosomes that contain a DNA construct that is transcribed to an RNA molecule in soybean plant cells to provide enhanced agronomic traits in such soybean plants and seeds for such plants and raw materials produced from such plants, and methods of making and using such molecules, chromosomes, cells, plants, seeds and raw materials.

SUMMARY OF THE INVENTION

This invention provides a non-natural transgenic chromosome in a soybean plant cell that includes a recombinant DNA construct that is transcribed to an RNA molecule that hybridizes under physiological conditions to and forms a cleavage-resistant duplex with a mature miR171miRNA or a transcript of a miR171-associated miRNA target gene having a recognition site for a mature miR171 miRNA. Such a cleavage-resistant duplex inhibits the function of at least one mature miR171 miRNA in a soybean cell. The non-natural transgenic chromosome of this invention is provided in a soybean plant cell in a non-natural, transgenic soybean plant having enhanced agronomic characteristics selected from a group consisting of increased pods per node, increased number of internodes and nodes, decreased average internode length, and a twisted stem phenotype as compared to a control.

The RNA molecule of this invention that hybridizes to a mature miR171 miRNA or its corresponding, complementary recognition site is designed with reference to a miR171 miRNA consensus sequence of UGAUUGAGCCGCGCCAAUAUC (SEQ ID NO: 91), with up to 6 mismatches and where the underlined nucleotide pair CG at positions 10 and 11 spans the nominal cleavage site, or of UUGAGCCGNGCCAAUAUCACN (SEQ ID NO: 92) with up to 6 mismatches and where the underlined nucleotide pair at GC at positions 10 and 11 spans the nominal cleavage site. The actual mature miR171 miRNA can have a deletion or an addition at either the 5' or 3' end. Specific miR171 miRNAs have a nucleotide sequence selected from the group consisting of SEQ ID NO: 17 through SEQ ID NO: 90.

In a broad aspect of the invention the non-natural transgenic chromosome has DNA that is transcribed to an RNA molecule that hybridizes to a mature miR171 miRNA to form a cleavage-resistant duplex between the RNA molecule and the miR171 miRNA where the cleavage site of the mature miR171 miRNA is between nucleotides that correspond to the nucleotides at positions 10 and 11 of the one of the above consensus RNA nucleotide sequences that best aligns with the nucleotide RNA sequence of the targeted mature miR171 miRNA. The RNA molecule of this invention has at least one nucleotide mismatch with the mature miR171 miRNA or its corresponding recognition site generally at positions 9-12 at the cleavage site of the mature miR171 miRNA. For instance, the RNA molecule designed to hybridize to a mature miR171 miRNA is not perfectly base paired with the mature miR171 miRNA (a) at least at position 11 at the cleavage site of the mature miR171 miRNA, or (b) at least at positions 10 and 11 at the cleavage site of the mature miR171 miRNA, or (c) includes at least one insertion nucleotide between nucleotides that are complementary to positions 10 and 11 at the cleavage site of the mature miR171 miRNA. An effective RNA molecule of this invention that hybridizes to a mature miR171 miRNA has at least three insertion nucleotides between the nucleotides of the RNA molecule that are complementary to positions 10 and 11 at the cleavage site of the mature miR171 miRNA. Useful transcribed RNA molecules of the invention have a nucleotide sequence of any of SEQ ID NO: 93 through SEQ ID NO: 118.

An RNA molecule transcribed from a recombinant DNA construct of this invention inhibits double-stranded RNA-mediated suppression of at least one mature miR171 miRNA. Such RNA molecules are provided in a non-natural soybean plant cell having a non-natural transgenic chromosome with a recombinant DNA construct.

In various other aspects, this invention provides a cleavage-resistant duplex between a transcribed RNA molecule and a mature miR171 miRNA. A cleavage-resistant duplex formed by a hybridized RNA molecule of this invention increases the expression of the miR171 miRNA target gene relative to expression in the absence of the RNA molecule. Such a cleavage-resistant duplex includes at least 6 base pairs or at least 10 base pairs in the recognition site of the mature miR171 miRNA. The cleavage-resistant duplex includes at least one mismatch at the cleavage site corresponding to positions 9, 10, 11 or 12 within the mature miR171 miRNA, or at least one insertion at a position in the RNA molecule and said recognition site corresponding to positions 10-12 within the mature miR171 miRNA, or a mismatch at a position corresponding to the 3' end of the recognition site. Examples of useful transcribed RNA molecules of the invention include those with a nucleotide sequence of any of the sequences of SEQ ID NO: 119 through SEQ ID NO: 143.

In yet a further aspect, a non-natural transgenic chromosome of this invention is contained in a non-natural transgenic soybean cell, in a live soybean plant, in a dead soybean plant, in a soybean seed, or in an industrial raw material, i.e., processed soybean seed.

In another aspect this invention provides a dead non-natural transgenic soybean plant that has increased pods per node as compared to the control, where the pods contain soybean seeds including a non-natural transgenic chromosome of this invention.

In a further aspect this invention provides a method of increasing the number of pods per node, or of increasing the number of internodes and nodes per plant, or of decreasing the distance between internodes, or of imparting a twisted stem phenotype in a soybean plant, as compared to a control, by providing in cells of the soybean a non-natural transgenic chromosome of this invention.

DETAILED DESCRIPTION OF THE INVENTION

Figure 1A:
FIGS. 1A-1B illustrates structures of transcribed RNA molecules that hybridize to a mature miR171 miRNA to form a cleavage-resistant duplex with a three-nucleotide insertion (labelled "bulge") corresponding to positions 10-11 cleavage site of the miR171 miRNA (FIG. 1A) or with two mismatches (labelled "mismatch") corresponding to positions 10 and 11 of the cleavage site of the miR171 miRNA (FIG. 1B).

This invention provides a non-natural transgenic chromosome in a soybean plant cell, wherein the non-natural transgenic chromosome has a recombinant DNA construct including DNA that is transcribed to an RNA molecule that under physiological conditions in a soybean plant cell hybridizes to and forms a cleavage-resistant duplex with either a mature miR171 miRNA or a transcript of a target gene having a recognition site for a mature miR171 miRNA, wherein the recognition site includes nucleotides complementary to nucleotides of the mature miR171 miRNA, whereby the function of the mature miR171 mRNA is inhibited in the soybean plant cell, and wherein the soybean plant cell is in a non-natural, transgenic soybean plant having enhanced agronomic characteristics selected from a group consisting of increased pods per node, increased number of internodes and nodes, decreased average internode length, and a twisted stem phenotype as compared to a control. The RNA molecule that hybridizes under physiological conditions in a soybean plant cell to form a cleavage-resistant RNA duplex with either a mature miR171 miRNA or a transcript of a target gene having a recognition site for a mature miR171 miRNA reduces the function of the mature miR171 miRNA. The non-natural transgenic chromosomes and the recombinant DNA constructs contained therein are useful for making a non-natural, transgenic soybean plant having enhanced agronomic characteristics selected from a group consisting of increased pods per node, increased number of internodes and nodes, decreased average internode length, and a twisted stem phenotype, as compared to a control.

The physiological conditions for the hybridizing in the practice of this invention are common field conditions during the growing season of a soybean plant. For example, the RNA molecule of this invention hybridizes to and forms a cleavage-resistant duplex with a mature miR171 miRNA in a cell of a soybean plant growing in a field under conditions including temperatures between about 20 to about 30 degrees Celsius and at a relative humidity between about 50 to about 100 percent.

A "control" generally means a plant that does not contain the non-natural transgenic chromosomes containing the recombinant DNA construct that transcribes to an RNA molecule of this invention that hybridizes under physiological conditions in a soybean cell to a mature miR171 miRNA or a transcript of a target gene having a recognition site for a mature miR171 miRNA to form a cleavage-resistant. A control can be a wild-type non-transgenic plant corresponding to the non-natural transgenic variety that contains the chromosome or recombinant DNA construct of the invention. A control can be a null variant progeny of a homozygous transgenic parent plant having the chromosome or recombinant DNA of the invention. A suitable control plant can be a non-transgenic plant of the parental line used to generate a transgenic plant, e. g., devoid of recombinant DNA and can in some cases is a progeny of a hemizygous transgenic plant line that does not contain the recombinant DNA, known as a negative segregant or negative isoline. In some embodiments, a control is a plant that contains a recombinant DNA construct encoding an RNA molecule of this invention, but where the recombinant DNA construct is not transcribed. A control is useful to identify and select a transgenic plant of this invention that has enhanced agronomic traits. Any soybean plant can be used in the practice of the methods of this invention for producing a transgenic chromosome, seed or plant having an enhanced agronomic trait.

The non-natural transgenic chromosomes of the invention can be prepared by inserting a recombinant DNA construct of this invention into a natural soybean chromosome or into an already transgenic soybean chromosome. Alternatively, the recombinant DNA that is transcribed to an RNA molecule of this invention can be placed on an artificial chromosome that is embedded in the nucleus of soybean plant cells using methods disclosed in Patent Application Publication US2009/0156793A1, US2008/0256669A1, and US2009/0209749 A1, which are incorporated herein by reference.

Recombinant DNA constructs useful in this invention include a promoter operable in soybean cells and operably linked to DNA that is transcribed to an RNA molecule designed to inhibit the function of a mature miR171 miRNA. In some embodiments the recombinant DNA constructs of this invention include DNA that is transcribed to multiple RNA molecules designed to inhibit more than one miRNA in the miR171 miRNA family or more than one gene having a miR171 miRNA recognition site, e. g., where segments of DNA that are transcribed to the multiple RNA molecules are arranged in tandem and expressed by action of a single promoter or separate promoters. Various promoters useful for expressing recombinant DNA constructs of this invention, include, but are not limited to, tissue-specific promoters and ubiquitous constitutive promoters. The recombinant DNA construct can also include other DNA, e. g., DNA encoding a transgene for expressing a protein or a selectable marker to facilitate transformation or a gene suppression element. In a recombinant DNA construct that is designed to also transcribe RNA coding for a protein or to non-coding RNA or both coding and non-coding RNAs, the DNA that is transcribed to an RNA molecule of this invention can be located in an intron or after the polyadenylation signal, to permit normal transcription of the other coding or non-coding DNA. A functional RNA molecule of this invention can be expressed as a separate RNA molecule, and a functional RNA molecule of this invention can also be embedded in other RNA, e. g., an RNA molecule of this invention can be embedded in the 3'-untranslated region of a protein-coding transcript. In one embodiment, a nucleotide spacer varying in size (e. g., 60 nucleotides or more than 60 nucleotides) can be inserted between the stop codon of a coding sequence and the DNA that transcribes to an RNA molecule of this invention; such a spacer sequence can increase the efficiency of the RNA molecule of this invention in inhibiting a mature miR171 miRNA. Useful chromosomes of this invention can also be obtained from transgenic soybean plants of this invention, e. g., for use in preparing other soybean plants by breeding techniques for transferring DNA from a chromosome in one plant to a chromosome in another.

A miRNA can be described by providing the nucleotide sequence of the mature miRNA, or of a miRNA precursor to the mature miRNA (such as the primary transcript of a miRNA gene or pri-miRNA), or of an intermediate in miRNA biogenesis such as a pre-miRNA, or of a cognate DNA (e. g., the DNA sequence encoding the mature miRNA, or genomic DNA of a MIR gene that is transcribed and processed to the mature miRNA, or DNA encoding a naturally occurring, e. g., endogenous, or an artificial miRNA precursor RNA molecule that is processed to the mature miRNA). Table 1 provides RNA sequences of mature miR171 miRNAs and the corresponding precursor miR171 miRNA that were identified from the publicly available miRBase database (mirbase.org). Additional miR171 genes and mature miRNAs and their targets are also described in Patent Application Publications US2005/0120415A1 and US2005/144669A1, which are incorporated by reference herein. The miR171 miRNA precursor RNAs are processed in the various plant species to the mature miR171 miRNAs.

With reference to Table 1, in column 1 there are sequence identifiers for miR171 RNA precursor sequences in the sequence listing (SEQ ID NOS: 1-16 for miR171 precursors), as well as the corresponding miRBase Accession Number Identifier (e. g., MI0000214) and organism identifier (e. g., athMIR171a) which includes a three-letter prefix indicating the species in which the mature miRNA was first identified. Column 2 shows the nucleotide sequence of the miR171 precursor. Column 3 is the sequence identifier (SEQ ID NOS: 17-32) for the mature miR171 miRNA. Column 4 shows the RNA sequence of the mature miR171 miRNA and the nucleotides in the precursor RNA from which the mature miR171 miRNAs were derived. The three letter prefix in the organism identifier is shown in parentheses following the species name: *Arabidopsis thaliana* (ath), *Otyza sativa* (osa), *Zea mays* (zma), *Sorghum bicolor* (sbi), *Medicago truncatula* (mtr), *Brassica napus* (bna), *Triticum aestivum* (tae), *Glycine max* (gma), *Solanum lycopersicum* (sly), *Brassica rapa* (bra), *Brassica oleracea* (bol).

The nucleotide sequences of mature miR171 miRNAs, SEQ ID NOS: 17-32 (Table 1) and SEQ ID NOS: 33-92 (Table 2) are used to design a recombinant DNA molecule that can be stably integrated into a chromosome of a soybean plant cell and be transcribed in that cell to an RNA molecule that hybridizes to a mature miR171 miRNA to form a cleavage-resistant duplex to reduce the function of the mature miR171 miRNA. The mature miR171 miRNAs for many of the plant species have a miR171 consensus sequence of UGAUUGAGCC<u>CG</u>CGCCAAUAUC (SEQ ID NO: 91) or of UUGAGCCGN<u>GC</u>CAAUAUCACN (SEQ ID NO: 92) where the typical cleavage site of the mature miR171 miRNA is indicated by the underscored nucleotides a positions 10 and 11.

TABLE 1

| miR171 precursor SEQ ID NO:, miRBase accession number and organism identifiers | miR171 precursor sequence | Mature miR171 SEQ ID NO: | Mature miR171 (nucleotide positions in miR171 precursor) |
|---|---|---|---|
| 1 | AUGAGAGAGUCCCUUUGAUAUUG-GCCU | 17 | (88-108) |
| MI0000214 | GGUUCACUCAGAUCUUACCUGAC-CACA | | UGAUUGAGCCGCG |
| athMIR171a | CACGUAGAUAUACAUUAUUCUCUC-UAG AUUAUCUGAUUGAGCCGCGC-CAAUAUC UCAGUACUCUCUCGU | | CCAAUAUC |
| 2 | UGCAAGGUAACGCGA-GAUAUUAGUGCG | 18 | (78-98) |
| MI0000989 | GUUCAAUCAAAUAGUCGUCCUC-UUAAC | | UUGAGCCGUGCCA |
| ath-MIR171b | UCAUGGAGAACGGUGUUGUUC-GAUUGA GCCGUGCCAAUAUCACGCG-GUAAACCA AAAAUGGCA | | AUAUCACG |
| 3 | GCGACGACGGGAUAUUGGGGCG-GUUCA | 19 | (70-90) |
| MI0001133 | AUCAGAAAGCUUGUGCUCCG-GAAGCGA | | UGAUUGAGCCGUG |
| osa-miR171b | GGAGCUCUACUCUUUUGAUUGAGC-CGU GCCAAUAUCACGUCGCAUC | | CCAAUAUC |

TABLE 1-continued

| miR171 precursor SEQ ID NO:, miRBase accession number and organism identifiers | miR171 precursor sequence | Mature miR171 SEQ ID NO: | Mature miR171 (nucleotide positions in miR171 precursor) |
|---|---|---|---|
| 4<br>MI0001138<br>osa-MIR171g | GACAUGGCAUGGUAUUGACUUGG-CUCAUCUCAGCAACAGCAAACUG-CAUGCAGCGCUGGAGGUGAGCCGAGCCAAUAU-CACUUCAUGUC | 20 | (59-79)<br>GAGGUGAGCCGAGCCAAUAUC |
| 5<br>MI0001155<br>osa-MIR171i | UAAAAAGAGGUAUUGGCGUGCCU-CAAUCCGAAGGCAUGGCUGAUUACAG-GCACCUCGACCGAUCUAGCGCAUGCAGC-CAUGUUUCUUGGAUUGAGCCGCGU-CAAUAUCUCUCCUUGCUUC | 21 | (88-108)<br>GGAUUGAGCCGCGUCAAUAUC |
| 6<br>MI0001570<br>sbi-MIR171e | AGGAGGAAGAAGACGACAUG-GCGUGGUAUUGUUUCGGCUCAUGUCCUUC-UUGCUUCGAGUCUGUCGUCGGAUUUUG-GAUGUGAUGUGAGCCGAACCAAUAUCACU-CAUGUAUUCUUCAUUCUGA | 22 | (85-105)<br>GUGAGCCGAACCAAUAUCACU |
| 7<br>MI0001854<br>sbi-miR171f | UGAGAGAAUAAGACGACAUG-GCGUGAUGUUGUUUCGGCUCAUGCAUAUC-CUUCUUGAGUGUAUCAUCAGGAAAGAGGC-GAUGAGCCGAACCAAUAUCACUCAU-GUAUUCUUCAUUCAUA | 23 | (72-92)<br>UGAGCCGUGCCAAUAUCACGA |
| 8<br>MI0001753<br>mtr-MIR171 | UGAAUUCCCCUCCGCUUUUUGAU-GUUGGCUUGUCUCAAUCAAAU-CAAAGUUCUUGAAAUUUGAGUUCUUUAGU-CUGAUUGAGUCGUGCCAAUAUCAUAUUAAGC-GAUAAAAGUC | 24 | (75-95)<br>UGAUUGAGUCGUGCCAAUAUC |
| 9<br>MI0001492<br>zma-miR171b | CGGGAUAUUGGCGCGGUUCAAUCA-GAAAGCUUGCGCUCCAGGCCCGAGGGG-CUCCACUCUUUGAUUGAGCCGUGC-CAAUAUCACG | 25 | (65-84)<br>UUGAGCCGUGCCAAUAUCAC |
| 10<br>MI0001835<br>zma-miR171c | GGGGAAUCGAAAAC-CUACGGGAUAUUGGUGCGGUUCAAUCAGAAAGC-UUGCGCUCCAAAGCCCAGGGGCUCCACUC-UUUGACUGAGCCGUGCCAAUAUCACGUC-CUCG | 26 | (79-99)<br>UGACUGAGCCGUGCCAAUAUC |
| 11<br>MI0001793<br>zma-MIR171f | UUGGUUGUUGGCUGAGAGAGUGC-GAUGUUGGCAUGGCUCAAUCAACUCGC-CGGCCGCGGGUGGCUUAUAGC-UUAAUUCUGCGCAUUCGAUCGAGGUGCGGGCGCA-GUG | 27 | (118-138)<br>UUGAGCCGUGCCAAUAUCACA |

TABLE 1-continued

| miR171 precursor SEQ ID NO:, miRBase accession number and organism identifiers | miR171 precursor sequence | Mature miR171 SEQ ID NO: | Mature miR171 (nucleotide positions in miR171 precursor) |
|---|---|---|---|
| 12<br>MI0006450<br>bna-MTR171a | UGGUCAAGCGAGAUAUUAGUGCG-GUUC<br>AAUCAAAUAGUCUCACUC-UUAGUUGAU<br>AGAGAUUGAUUUUGUUC-GAUUGAGCCG<br>UGCCAAUAUCACGCAUAUAACCA | 28 | (65-85)<br>UUGAGCCGUGCCA<br>AUAUCACG |
| 13<br>MI0006451<br>bna-miR171b | GGUAACGCGAGAUAUUAGUGCG-GUUCA<br>AUCAAAUAGUCGUGUUCUCAC-UUGAUA<br>GAGAUCGGUUUUGUUCGAUUGAGC-CGU<br>GCCAAUAUCACGCGUCAACC | 29 | (22-42)<br>UAUUGGUGCGGUU<br>CAAUGAGA |
| 14<br>MI0006452<br>bna-MIR171c | GCGAGAUAUUAGUGCGGUUCAAU-CAAA<br>UAGUCGUACUCUUAGCUAUUAGA-GAUC<br>GGUUUUGUUCGAUUGAGCCGUGC-CAAU<br>AUCACGC | 30 | (75-94)<br>UUGAGCCGCGCCA<br>AUAUCAC |
| 15<br>MI0005771<br>bna-MIR171g | GAUAUUGGCCUGGUUCACUCA-GAUUAC<br>ACACGUACUAUAUGCAUUCUC-UUAGUU<br>AUCUGAUUGAGCCGCGCCAAUAUCUC | 31 | (62-82)<br>CGAGCCGAAUCAA<br>UAUCACUC |
| 16<br>MI0006175<br>tae-MIR171 | UGGAAUGGUCACUAUGAUGUUGG-CUCG<br>ACUCACUCAGACCACGCCUGCCG-GCCG<br>GCCGUAGCCAUGCAUCUGCAUGCG-GUG<br>GUGGCUCUGAUUGAGCCGUGC-CAAUAU | 32 | (87-107)<br>UGAUUGAGCCGUG<br>CCAAUAUC |

With reference to Table 2 there is listed the sequences of the mature miR171 miRNAs from several plant species to illustrate both the high conservation among miRNAs in a given miRNA family and the sequence variability of mature miRNAs within a family. The mature miR171 miRNA family members were selected from sequences of small RNAs isolated from the indicated plant species. In Table 2, column 1 provides a reference to a sequence identifier (SEQ ID NO:) in the sequence listing (SEQ ID NO: 33-92), column 2 provides the nucleotide sequence of the mature miR171 miRNA, column 3 provides the nucleotide length for the mature miRNA, and column 4 provides the specific miR171 name (e. g., ath-miR171a), which includes a three-letter prefix for the organism from which the mature miRNA was first identified: *Arabidopsis thaliana* (ath), *Oryza sativa* (osa), *Zea mays* (zina), *Medicago truncatula* (mtr), *Brassica napus* (bna), *Vitis vinifera* (vvi), *Populus trichocarpa* (ptc) and *Selaginella rnoellendorffii* (smo).

TABLE 2

| SEQ ID NO: | Mature naiP171 miRNA | Length (nucleotides) | annotation |
|---|---|---|---|
| 33 | UGAUUGAGCCGGGCCAAUAUC | 21 | ath-miR171a |
| 34 | CAUUGAGCCGUGCCAAUAUCACGC | 24 | ath-miR171b |
| 35 | AUUGAGCCGUGUCAAUAUC | 19 | ath-miR171 |
| 36 | UGAUUGAGCCGUGUCAAUAUC | 21 | ath-miR171 |
| 37 | UGAUUGAGCCGUGACAAUAUC | 21 | ath-miR170 |
| 38 | UGAUUGAGCCGCGCCAAUAU | 20 | zma miR171a |
| 39 | UGACUGAGCCGUGCCAAUAUC | 21 | zma-miR171c |
| 40 | UGAUUGAGCCGUGCCGAUAUC | 21 | osa-miR171b |
| 41 | AUUGAGCCGUGUCAAUAUC | 19 | osa-miR171b |
| 42 | UGAUUUAGCCGUGCCAAUAUC | 21 | osa-miR171b |
| 43 | UGAUUGAGCCGUGCCAAUA | 19 | osa-miR171b |
| 44 | UGAUUGAACCGUGCCAAUAUC | 21 | osa-miR171b |
| 45 | UGAUUAAGCCGUGCCAAUAUC | 21 | osa-miR171b |
| 46 | UGAUUGAGCCGUUGCCAAUAUUC | 23 | osa-miR171b |

TABLE 2-continued

| SEQ ID NO: | Mature naiP171 miRNA | Length (nucleotides) | annotation |
|---|---|---|---|
| 47 | UGAUUGAACCGUGCCAAUAUC | 21 | osa-miR171b |
| 48 | UGAUUGAGCCGUUCCAAUAUC | 21 | osa-miR171b |
| 49 | UGAUUGAGACGUGCCAAUAUC | 21 | osa-miR171b |
| 50 | UGAUUGAGCCGUGCCAAUACC | 21 | osa-miR171b |
| 51 | UGAUUGAGCCGUGCAAAUAUC | 21 | osa-miR171b |
| 52 | UGAUUAAGCCGUGCCAAUAUC | 21 | osa-miR171b |
| 53 | UGAUUGAGCCGUCCCAAUAUC | 21 | osa-miR171b |
| 54 | UGAUUGAGCCGUGCUAAUAUC | 21 | osa-miR171b |
| 55 | UGAUUGAGCAGUGCCAAUAUC | 21 | osa-miR171b |
| 56 | UGAUUGAUCCGUGCCAAUAUC | 21 | osa-miR171b |
| 57 | UGAUAGAGCCGUGCCAAUAUC | 21 | osa-miR171b |
| 58 | UGAUUGAGCCGUGCCUAUAUC | 21 | osa-miR171b |
| 59 | UGAUUGAGCUGUGCCAAUAUC | 21 | osa-miR171b |
| 60 | UGAUUGAGCCGUGCCAAUAUA | 21 | osa-miR171b |
| 61 | UGAUUGAGCCGUGCCAGUAUC | 21 | osa-miR171b |
| 62 | UGAUUGAGCCGUGCCCAUAUC | 21 | osa-miR171b |
| 63 | UGAUUGAGCCGUGCCAAUAUCUGG | 24 | osa-miR171b |
| 64 | CGAUUGAGCCGUGCCAAUAUC | 21 | osa-miR171b |
| 65 | UUAUUGAGCCGUGCCAAUAUC | 21 | osa-miR171b |
| 66 | UGAUUGAGCCGUGCCGAUA | 19 | osa-miR171b |
| 67 | UGAUUGAGCCGUGCCAAUAUU | 21 | osa-miR171b |
| 68 | CAUUGAGCCGUGCCAAUAUCA | 21 | osa-miR171b |
| 69 | UGAUUGAGCCGUGCCAAUAUCC | 22 | osa-miR171b |
| 70 | UGAUUGAGCCGUGCCACUAUC | 21 | osa-miR171b |
| 71 | AUCUGAUUGAGCCGUGCCAAUAUC | 24 | osa-miR171b |
| 72 | UUGAUUGAGCCGUGCCAAUAUC | 22 | osa-miR171b |
| 73 | UCUGAUUGAGCCGUGCCAAUAUC | 23 | osa-miR171b |
| 74 | CUGAUUGAGCCGUGCCAAUAUC | 22 | osa-miR171b |
| 75 | UGAUUGAGCCGUGCCAAUCUC | 21 | osa-miR171b |
| 76 | UGAUUGAGCCGUGCCAAUAUUUU | 23 | osa-miR171b |
| 77 | UGAUUGAGCCGUGCCAAUUUC | 21 | osa-miR171b |
| 78 | UGCUUGAGCCGUGCCAAUAUC | 21 | osa-miR171b |
| 79 | UGAUUGAGUCGUGCCAAUAUC | 21 | mtr-miR171b |
| 80 | UGAUUGAGUCGUGCCAAUAUC | 21 | mtr-miR171 |
| 81 | UGAUUGAUCCGCGCCAAUAUCU | 21 | bna-miR171 |
| 82 | UGAUUGAGCCGUGCCAAUAUUU | 22 | bna-miR171g |
| 83 | UGAUUGAGCCGUGCCAAUAUCU | 22 | bna-miR171g |
| 84 | UUUGAUUGAGCCGCGUCAAUA | 21 | vvi-MIR171b |
| 85 | AUUGAGCCGCGUCAAUAUC | 19 | vvi-miR171b |
| 86 | UGAGCCGCGCCAAUAUCACAU | 21 | ptc miR171a |
| 87 | AGAUUGAGCCGCGCCAAUAUC | 21 | ptc-miR171c |
| 88 | UAGAUUGAGCCGUGCCAAUAUC | 22 | ptc-miR171c |
| 89 | GGAUUGAGCCGUGCCAAUAUC | 21 | ptc-miR171k |
| 90 | UUGAGCCGUGCCAAUAUCACU | 21 | smo-miR171a |
| 91 | UGAUUGAGCCGCGCCAAUAUC | 21 | consensus |
| 92 | UUGAGCCGNGCCAAUAUCACN | 21 | consensus |

In one aspect of the invention an RNA molecule that hybridizes to and forms a cleavage-resistant duplex to reduce the function of a mature miR171 miRNA is designed to hybridize with at least one mature miR171 miRNA across the cleavage site of the mature miR171 miRNA, but can hybridize along the full length of the mature miR171 miRNA or extend beyond the 5' and 3' ends of the mature miR171 miRNA. The RNA molecule is at least 11 nucleotides and typically between 19 and 26 contiguous RNA nucleotides or larger and is sufficiently complimentary to the mature miR171 miRNA to form the cleavage-resistant duplex. Such RNA molecules of this invention are not perfectly base-paired with the mature miR171 miRNA at the cleavage site. The cleavage site is located within the mature miRNA typically located between nucleotides 10 and 11 of the mature miRNA. In some embodiments, the mature miR171 miRNA has a consensus RNA nucleotide sequence of UGAUUGAGCCGCGCCAAUAUC (SEQ ID NO: 91) or of UUGAGCCGNGCCAAUAUCACN (SEQ ID NO: 92), where the sequence of the mature miR171 miRNA has up to 6 mismatches with the miR171 consensus sequence with which it best aligns (either SEQ ID NO: 91 or SEQ ID NO: 92) and includes up to 2 nucleotide additions or up to 2 nucleotide deletions at the 5' terminus, the 3' terminus, or both the 5' and 3' termini of the mature miR171 miRNA. In these embodiments, the cleavage site of the mature miR171 miRNA is between nucleotides that correspond to the nucleotides at positions 10 and 11 of the miR171 consensus sequences that best aligns with the nucleotide RNA sequence of the mature miR171 miRNA, and the RNA molecule is not perfectly base-paired with the mature miR171 miRNA (a) at least at position 11 at the cleavage site, (b) at least at positions 10 and 11 at the cleavage site, or (c) includes at least one insertion nucleotide between the nucleotides that are complementary to positions 10 and 11 at the cleavage site. In other embodiments the RNA molecule includes at least three insertion nucleotides inserted between the nucleotides that are complementary to positions 10 and 11 at the cleavage site. Specific embodiments of the RNA molecule of this invention include an RNA molecule having an RNA nucleotide sequence selected from the group consisting of SEQ ID NO: 93 through SEQ ID NO: 118.

Figure 1B:
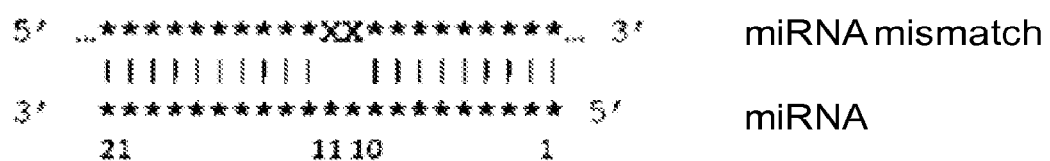

Exemplary transcribed RNA molecules of the invention that hybridize to a mature miR171 miRNA to form a cleavage-resistant duplex comprise an RNA nucleotide sequence of any of SEQ ID NOS: 93-118, i. e., a nucleotide sequence that is generally complementary to the nucleotide sequence of the target mature miR171 miRNA except at the cleavage site of the mature miR171 miRNAs. With reference to FIG. 1 there is shown two structures of transcribed RNA molecules that are effective in the practice of this invention and that can hybridize to a mature miR171 miRNA with a three-nucleotide insertion ("bulge") corresponding to positions 10-11 at the cleavage site of the mature miR171 miRNA (FIG. 1A) or with two mismatches ("mismatch") corresponding to nucleotide positions at 10 and 11 at the cleavage site of the mature miR171 miRNA (FIG. 1B). Sequence modifications to the RNA molecules of this invention where the modification is at one or more nucleotides corresponding to the nucleotides at or near the mature miR171 miRNA cleavage site can affect the degree of functional impairment of the mature miR171 miRNAs and are useful for providing variability in the phenotype in the plant. The interactions between the mature miR171 miRNA and the RNA molecule of this invention can be varied by the number or type of mismatches between the mature miR171 and the RNA molecule, e. g., one to six nucleotide insertions (mismatches) can be used in the sequence of the RNA molecule at nucleotide positions corresponding to the cleavage site of the mature miR171 miRNA, thereby creating "bulges" of varying size between the RNA molecule of this invention and the mature miR171 miRNA. For instance, miRNA function is less affected by a single mismatch at position 11 than by a mismatch at both positions 10 and 11 than by an insertion of three nucleotides between positions 10 and 11. The ability to modify the degree of inactivation provides a means to systematically titrate the endogenous miR171 miRNA activity for achieving a desired level of the regulation of miR171 target mRNAs.

Table 3 discloses the design of examples of RNA molecules that are useful in the practice of this invention and which hybridize to and form a cleavage-resistant duplex with an endogenous mature miR171 miRNA. In specific embodiments the RNA molecule of this invention can have the RNA nucleotide sequence of any of SEQ ID NOS: 93-118, as referenced in Table 3. With reference to Table 3, column 1 provides a reference to a sequence ("SEQ ID NO:") in the sequence listing (SEQ ID NOS: 93-118), column 2 shows the nucleotide sequence of an RNA molecule designed to hybridize to miR171 miRNA to form a cleavage-resistant duplex, column 3 shows the sequence identifiers ("SEQ ID NOS:") for the mature miR171 miRNA (shown above in the table cell) and the RNA molecule that hybridizes to the mature miR171 miRNA (shown below in the table cell), column 4 shows an alignment between the mature miR171 miRNA (above) in a 3' to 5' direction and the nucleotides of miR171 RNA molecule that hybridized (below) in a 5' to 3' direction.

TABLE 3

| SEQ ID NO: | Sequences for miR171 RNA molecule that hybridizes to mature miR171 miRNA | SEQ ID NO: | Alignment between mature miR171 miRNA (3' to 5' direction) and sequence of miR171 RNA molecule (5' to 3' direction) |
|---|---|---|---|
| 93 | GAUAUUGGCGCAUAGGCUCAAUCA | 17<br>93 | CUAUAACCGCG---CCGAGUUAGU<br>GAUAUUGGCGCAUAGGCUCAAUCA |
| 94 | GAUAUUGGCGUCGCUCAAUCA | 17<br>94 | CUAUAACCGC--CGAGUUAGU<br>GAUAUUGGCGUCGCUCAAUCA |
| 95 | AAUAUUGGUGUCAAGCUCAAUCA | 17<br>95 | CUAUAACCGCGC---CGAGUUAGU<br>AAUAUUGGUGUCAAAGCUCAAUCA |
| 96 | GGUGAUAUUGGCUACACGGCUCAA | 18<br>96 | GCACUAUAACCG---UGCCGAGUU<br>GGUGAUAUUGGCUACACGGCUCAA |
| 97 | AAAUAUUGGUGUCAAAGCUCAAUCA | 81<br>97 | UCUAUAACCGCGC---CGAGUUAGU<br>AAAUAUUGGUGUCAAAGCUCAAUCA |
| 98 | AGAUUUUUGUGUGCAGGCUCAAUCA | 81<br>98 | UCUAUAACCGCGC---CGAGUUAGU<br>AGAUUUUUGUGUGCAGGCUCAAUCA |
| 99 | UUUGUUGGCACAAGUGCUCAAUCA | 19<br>99 | CUAUAACCGUGC---CGAGUUAGU<br>UUUGUUGGCACAAGUGCUCAAUCA |
| 100 | GAUAUUGGCGCAAUAGGCUCAAUCA | 19<br>100 | CUAUAACCGUG----CCGAGUUAGU<br>GAUAUUGGCGCAAUAGGCUCAAUCA |
| 101 | GAUAUUGACGUGGCUCAAUCA | 19<br>101 | CUAUAACCG--CCGAGUUAGU<br>GAUAUUGACGUGGCUCAAUCA |
| 102 | GAUAUUAGUGUGGCUCAAUCA | 19<br>102 | CUAUAACC---CCGAGUUAGU<br>GAUAUUAGUGUGGCUCAAUCA |
| 103 | GGGCUUGGCUUUCUGGCUCACCUC | 20<br>103 | CUAUAACCGAG---CCGAGUGGAG<br>GGGCUUGGCUUUCUGGCUCACCUC |
| 104 | GAUAAUUGUUAUGCUCACCUC | 20<br>104 | CUAUAACCGA--CGAGUGGAG<br>GAUAAUUGUUAUGCUCACCUC |
| 105 | CGUAGUGGCUGGGCUCACCUC | 20<br>105 | CUAUAACCGA-CCGAGUGGAG<br>CGUAGUGGCUGGGCUCACCUC |
| 106 | GAUGUUGACACACCGGCUCAAUCC | 21<br>106 | CUAUAACUGCG---CCGAGUUAGG<br>GAUGUUGACACACCGGCUCAAUCC |
| 107 | GAUAUAGCUGUGCCUGCUCAAUCC | 21<br>107 | CUAUAACUGCGC---CGAGUUAGG<br>GAUAUAGCUGUGCCUGCUCAAUCC |
| 108 | GAUGUUGGCACUCCUGCUCAAUCC | 21<br>108 | CUAUAACUGCGC---CGAGUUAGG<br>GAUGUUGGCACUCCUGCUCAAUCC |
| 109 | AUAUUGGUGUCAAAGCUCAAUCA | 38<br>109 | UAUAACCGCGC---CGAGUUAGU<br>AUAUUGGUGUCAAAGCUCAAUCA |
| 110 | GUGAUAUUGGCUACACGGCUCAA | 25<br>110 | CACUAUAACCG---UGCCGAGUU<br>GUGAUAUUGGCUACACGGCUCAA |
| 111 | GAAGUAUUGGCCAGACGGCUCAA | 25<br>111 | CACUAUAACCG---UGCCGAGUU<br>GAAGUAUUGGCCAGACGGCUCAA |
| 112 | UUGAGGUUGGGCUCGCGGCUCAA | 25<br>112 | CACUAUAACC---GUGCCGAGUU<br>UUGAGGUUGGGCUCGCGGCUCAA |
| 113 | GAAAUUUGUACAUAGGCUCAGUCA | 26<br>113 | CUAUAACCGUG---CCGAGUCAGU<br>GAAAUUUGUACAUAGGCUCAGUCA |
| 114 | GGUGAUAUUGGCUACACGGCUCAA | 27<br>114 | ACACUAUAACCG---UGCCGAGUU<br>GGUGAUAUUGGCUACACGGCUCAA |
| 115 | GAUGUUGUCACGCACACUCAAUCA | 24<br>115 | CUAUAACCGUGC---UGAGUUAGU<br>GAUGUUGUCACGCACACUCAAUCA |
| 116 | GUGUGUUUUUGGGCGCGCGGCUCA | 86<br>116 | UACACUAUAACC---GCGCCGAGU<br>GUGUGUUUUUGGGGCGCGCGGCUCA |

TABLE 3-continued

| SEQ ID NO: | Sequences for miR171 RNA molecule that hybridizes to mature miR171 miRNA | SEQ ID NO: | Alignment between mature miR171 miRNA (3' to 5' direction) and sequence of miR171 RNA molecule (5' to 3' direction) |
|---|---|---|---|
| 117 | GGUGUUGCCGCCG CGGCUCAAUCU | 87 117 | CUAUAACCGCG---CCGAGUUAGA GGUGUUGCCGCCGCGGCUCAAUCU |
| 118 | UAUGUUUGCGUAU GGGCUCAAUCC | 89 118 | CUAUAACCGCG---CCGAGUUAGG UAUGUUUGCGUAUGGGCUCAAUCC |

Another aspect of the invention provides RNA molecules that hybridize to a transcript of a target gene having a recognition site for a mature miR171 miRNA, wherein the recognition site includes nucleotides complementary to nucleotides of the mature miR171 miRNA, to form a cleavage-resistant duplex that reduces the function of the mature miR171 miRNA. Such cleavage resistance is believed to be resistance to cleavage by an RNase III ribonuclease within or in the vicinity of the duplex or hybridized segment that is formed by binding of an RNA molecule of this invention to a mature mir171 miRNA recognition site in the transcript of a gene targeted for enhanced expression. The specific binding of a RNA molecule of this invention to of the transcript of a miR171 miRNA-regulated target gene occurs within or in the vicinity of the miR171 miRNA recognition site found in that transcript in a manner that reduces or prevents miR171 miRNA-mediated cleavage of the transcript by competing with the mature miR171 miRNA for binding to the recognition site and thus imparting to the transcript resistance to cleavage, e.g., by an RNase III ribonuclease. In some embodiments the duplex or hybridized segment formed between the RNA molecule of this invention and the target gene transcript extends over the full miR171 miRNA recognition site. In other embodiments the duplex is formed partially over the recognition site and partially over other RNA in the target gene transcript (e. g., partially over nucleotides in the transcript that are adjacent to the recognition site). In other embodiments the duplex does not form within the recognition site but only within the target gene transcript sufficiently close to the recognition site to interfere with binding by the miR171 miRNA. Thus, the RNA molecules of this invention are useful for enhancing the expression of one or more target genes having miR171 recognition sites.

In one embodiment, the general design of an RNA molecule that hybridizes to a transcript of a target gene having a recognition site for a mature miR171 miRNA includes an RNA sequence that is essentially identical to the RNA sequence of a mature miR171 miRNA except in the region of the cleavage site, e. g., with mismatches, insertions or deletions in the region of the cleavage site. The RNA molecule can extend beyond the recognition site in either the 5' or the 3' direction or in both directions. Alternatively, the design of an RNA molecule that hybridizes to a transcript of a target gene having a recognition site for a mature miR171 miRNA includes nucleotides that hybridize to part of the recognition site, including the cleavage site (with mismatches, insertions or deletions) or not including the cleavage site, i. e., extending from the border of the cleavage site into the gene transcript. Such an RNA molecule typically forms a duplex with at least 6 to 10 base pairs in the miR171 miRNA recognition site. In still other embodiments, the RNA molecule optionally includes additional nucleotides that are not base-paired to the RNA transcript of the targeted gene. In specific aspects of the invention the chromosome of this invention is designed to have DNA that is transcribed to an RNA molecule that hybridizes to and forms a cleavage-resistant duplex with a transcript of a target gene having a recognition site for a mature miR171 miRNA, wherein the cleavage resistant duplex includes (a) at least one mismatch between the RNA molecule and the miR171 miRNA recognition site corresponding to positions 9, 10, 11 or 12 (in 3' to 5' direction) of the mature miR171 miRNA, or (b) at least one insertion or deletion in the RNA molecule corresponding to positions 10, 11 or 12 (in 3' to 5' direction) of the mature miR171 miRNA, or (c) a mismatch corresponding to the 3' end of the recognition site where the 5' nucleotide of a miR171 miRNA is typically a U, thus the RNA molecule can have a C, G, or A at the position corresponding to the 3' end of the recognition site. Additional methods on how to make and use an RNA molecule that under physiological conditions in a plant cell hybridizes to and forms a cleavage-resistant duplex with a transcript of a target gene having a recognition site for a mature miRNA are disclosed in Patent Application Publication PCT/US2009/49392, which is incorporated herein by reference.

Exemplary RNA molecules that form cleavage-resistant duplexes with a transcript of a target gene having a recognition site for a mature miR171 miRNA include the molecules having the RNA nucleotide sequence of SEQ ID NO:119 to SEQ ID NO:143, more particularly illustrated in Table 4. For example, the RNA molecule with the nucleotide sequence of SEQ ID NO: 119 is designed to reduce or prevent the function of at least one endogenous mature miR171 miRNA derived from nucleotide positions 88-108 from the miR171 miRNA precursor sequence from *Arabidopsis* miR171a (SEQ ID NO: 1) which corresponds to the mature miR171 miRNA (SEQ ID NO: 17). More specifically the RNA molecule represented by SEQ ID NO:119 has mismatching nucleotides CG indicated in bold lower case (cg) as compared to nucleotides GC at positions 11 and 12 in the mature miR171 miRNA. Table 1 illustrates various miR171 miRNA precursor sequences and their corresponding mature miR171 miRNAs, which can be used to design RNA molecules of this invention that inhibit in a specific manner mature miR171 miRNAs from cleaving their target transcripts. Table 4 illustrates embodiments of these RNA molecules which include mismatches (SEQ ID NOS: 119-130) or deletions (SEQ ID NOS: 131-142) at nucleotide positions 9-12. With reference to Table 4 there is listed the sequences of the RNA molecules designed specifically to miR171a miRNAs target genes. In Table 4, column 1 provides a reference to a sequence identifier (SEQ ID NO:) in the sequence listing (SEQ ID NO: 119-143), and column 2 provides the nucleotide RNA sequence of the RNA molecule where lower case, bolded letters indicate a nucleotide mismatch and dashes indicate nucleotide deletions and Ns indicate nucleotides that are complementary to the RNA transcript outside of the miR171 miRNA recognition site.

TABLE 4

| SEQ ID NO: | RNA molecule designed to block cleavage of miR171 target gene |
|---|---|
| 119 | UGAUUGAGCCcgGCCAAUAUC |
| 120 | UGAUUGAGCCGCGCCAAUAUg |
| 121 | UGAUUGAGgCGCGCCAAUAUC |

TABLE 4-continued

| SEQ ID NO: | RNA molecule designed to block cleavage of miR171 target gene |
|---|---|
| 122 | UGAUUGAGCgGCGCCAAUAUC |
| 123 | UGAUUGAGCCcCGCCAAUAUC |
| 124 | UGAUUGAGCCGgGCCAAUAUC |
| 125 | UGAUUGAGggGCGCCAAUAUC |
| 126 | UGAUUGAGCcgCGCCAAUAUC |
| 127 | UGAUUGAGCCgcGCCAAUAUC |
| 128 | UGAUUGAGggcCGCCAAUAUC |
| 129 | UGAUUGAGggcgGCCAAUAUC |
| 130 | UGAUUGAG-CGCGCCAAUAUC |
| 131 | UGAUUGAGCCGCGCCAAUAUC |
| 132 | UGAUUGAGC-GCGCCAAUAUC |
| 133 | UGAUUGAGCC-CGCCAAUAUC |
| 134 | UGAUUGAGCCG-GCCAAUAUC |
| 135 | UGAUUGAG—GCGCCAAUAUC |
| 136 | UGAUUGAGC—CGCCAAUAUC |
| 137 | UGAUUGAGCC—GCCAAUAUC |
| 138 | UGAUUGAG---CGCCAAUAUC |
| 139 | UGAUUGAGC---GCCAAUAUC |
| 140 | UGAUUGAG----GCCAAUAUC |
| 141 | GAGCCcgGCCAAUAUg |
| 142 | UGAUUGAGCCcgGCCAA |
| 143 | NNNNUGAUUGAGCC |

The RNA molecule that hybridizes to a mature miR171 miRNA or a transcript of a target gene having a recognition site for a mature miR171 miRNA to form a cleavage-resistant duplex is produced by recombinant DNA that is stably incorporated into a chromosome which can be located in a non-natural transgenic soybean cell, plant, seed, or plant part or in industrial raw material(s) derived from non-natural, transgenic soybean crushed seeds or plant parts. The industrial raw material including the non-natural transgenic chromosomes of this invention can be processed into food and feed products, biodiesels, epoxidized oils, saponified oils, lotions, lubricants, solvents, coatings, and resin products.

Aspects of the invention are provided by transgenic plants, seed and plant cells that are produced by a method including the steps of (a) producing non-natural transgenic soybean plant cells by introducing into a chromosome in the genome of a soybean plant cell a recombinant DNA molecule that is transcribed to an RNA molecule that hybridizes under physiological conditions to form a cleavage-resistant duplex with a mature miR171 miRNA or a transcript of a target gene having a recognition site for a mature miR171 miRNA, (b) regenerating a non-natural transgenic plant from the transgenic soybean plant cells, and optionally producing non-natural transgenic progeny soybean plants, and (c) screening the population of transgenic soybean plants to select a non-natural transgenic soybean plant having an enhanced agronomic trait (compared to a control plant) imparted by the recombinant DNA molecule. A "transgenic chromosome, cell or plant" means a chromosome, cell or plant that contains the recombinant DNA construct of this invention stably integrated into the chromosome or in the genome of the cell or plant, typically as a single copy and heritable in progeny plants, seeds and cells. A transformed plant cell and transgenic progeny resulting from transferring the stably integrated recombinant DNA into other soybean plant lines by crossing or introgression.

A further aspect of the invention is a method to increase the number of pods per node in a non-natural transgenic soybean plant by regulating the activity of endogenous mature miR171 miRNA (and thereby regulating the miR171 target genes) by expressing in a cell of the transgenic soybean plant a recombinant DNA construct that is transcribed to an RNA molecule that under physiological conditions in the cell hybridizes to and forms a cleavage-resistant duplex with a mature miR171 miRNA molecule or a transcript of a target gene having a recognition site for a mature miR171 miRNA. The production of RNA molecules that hybridize to endogenous mature miR171 miRNAs or to a transcript of a target gene having a recognition site for a mature miR171 miRNA in soybean plant cells reduces the miR171 activity against target messenger RNA (mRNA), e.g., of endogenous target genes of the mature miR171 miRNA. The production of RNA molecules of this invention in soybean plant cells enables the inactivation or at least reduction in function of at least one endogenous mature miR171 miRNA and thus inhibits the mature miRNA from regulating its natural target mRNA proteins. The production of RNA molecules of this invention provides increased activity of miR171-regulated proteins.

Soybean Transformation Methods

Methods for transforming plant cells with recombinant DNA are known in the art. In particular, *Agrobacterium tumefaciens*-based plant transformation methods for stable introgression of recombinant DNA constructs into soybean chromosomes are useful in the practice of stably integrating a recombinant DNA construct into a soybean chromosome to produce a non-natural transgenic chromosome of this invention. Such recombinant DNA constructs include one or more expression cassettes each including a promoter operably linked to DNA, e. g., DNA that transcribes to an RNA molecule that hybridizes to a mature miR171 miRNA. *Agrobacterium*-mediated transformation methods and materials for preparing the transgenic chromosomes, cells, and plants of this invention are disclosed in U.S. Pat. Nos. 5,731,179; 5,824,877; 7,002,058 and in Patent Application Publications US2005/0183170A1; US2003/110532A1 and US 2009/0138985A1, all of which are incorporated herein by reference. The DNA to be integrated can be advantageously flanked by T-DNA border elements from an *Agrobacterium tumefaciens* tumor inducing plasmid. The recombinant DNA constructs including expression cassettes (e. g., a promoter and DNA to be transcribed such as the DNA that is transcribed to an RNA molecule of this invention and DNA encoding a selectable marker) that can be transferred into a plant cell and can be present on one transformation vector in a bacterial strain being utilized for transformation. In another embodiment, the multiple recombinant DNA constructs can be present on separate transformation vectors.

In the practice of transformation DNA is typically introduced into only a small percentage of target plant cells. Selectable marker genes are used to provide an efficient system for identification of those cells that are stably transformed with a recombinant DNA molecule. Selectable markers confer resistance to a selective agent such as an antibiotic or an herbicide. A number of selectable marker genes are known in the art and can be used in the present invention. Selectable marker genes conferring tolerance to antibiotics like kanamycin and paromomycin (nptII), hygromycin B (aph IV), spectinomycin (aadA, U.S. Patent Publication 2009/0138985A1) and gentamycin (aac3 and aacC4) or tolerance to glyphosate (e. g., 5-enolpyruvylshikimate-3-phosphate synthase (EPSPS), U.S. Pat. Nos. 5,627,061; 5,633,435; 6,040,497; 5,094,945), tolerance to sulfonyl herbicides (e. g., acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. Nos. 6,225,105; 5,767,366; 4,761,373; 5,633,437; 6,613,963; 5,013,659; 5,141,870; 5,378,824; 5,605,011); tolerance to bialaphos or phosphinothricin or derivatives (e. g., phosphinothricin acetyltransferase (bar)) tolerance to phosphinothricin or glufosinate (U.S. Pat. Nos. 5,646,024; 5,561,236; 5,276,268; 5,637,489; 5,273,894); tolerance to dicamba (dicamba monooxygenase, Patent Application Publications US2003/0115626A1), or tolerance to sethoxydim (modified acetyl-coenzyme A carboxylase for conferring tolerance to cyclohexanedione (sethoxydim)), and tolerance to aryloxyphenoxypropionate (haloxyfop, U.S. Pat. No. 6,414,222).

The promoters used in the expression cassettes of the recombinant DNA of this invention can include "enhancer" DNA that assists in elevating expression of the recombinant DNA. Enhancers are often found 5' to the start of transcription in a promoter that functions in eukaryotic cells, but can often be inserted upstream (5') or downstream (3') to the coding sequence. In some instances, these 5' enhancing elements are introns. Such enhancers are known in the art. Useful enhancers are the 5' introns, for example, *Arabidopsis* actin 7 intron. Other particularly useful enhancers are the 5' introns of the rice actin 1 (U.S. Pat. No. 5,641,876) and rice actin 2 genes, and the CaMV 35S enhancer (U.S. Pat. Nos. 5,359,142 and 5,196,525) or an octopine synthase enhancer (U.S. Pat. No. 5,290,924). The promoter can also be followed by non-translated leader DNA derived from unrelated promoters as disclosed in U.S. Pat. No. 5,362,865. The promoter can also be non-translated leader DNA derived from unrelated promoters as disclosed in U.S. Pat. No. 5,362,865. Non-translated leader DNA can include maize and *petunia* heat shock protein leaders (U.S. Pat. No. 5,362,865), plant virus coat protein leaders, plant Rubisco leaders, GmHsp (U.S. Pat. No. 5,659,122), and Ph. DnaK (U.S. Pat. No. 5,362,865).

Expression cassettes of this invention can also include a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". Expression cassettes, e. g., for selectable markers can also include a transit peptide for targeting a gene to a plant organelle, particularly to a chloroplast, leucoplast or other plastid organelle. For descriptions of the use of chloroplast transit peptides see U.S. Pat. Nos. 5,188,642 and 5,728,925.

The insertion of recombinant DNA into a soybean chromosome to produce transgenic soybean cells by *Agrobacterium*-mediated transformation can be practiced using a plasmid vector with the genetic elements as shown in Table 5, where column 1 describes the function of the segment of the plasmid, column 2 provides a short description of a discrete genetic element and column 3 provides a more detailed description of the element. Transgenic soybean plants having the transgenic chromosome of this invention and grown to maturity are observed to have enhanced traits as compared to a control plant and are used to produce transgenic seed of this invention. A transgenic event results from the random insertion of recombinant DNA into a unique locus in a specific chromosome in a transgenic soybean cell. When each such unique transgenic cell is regenerated into a genetically unique transgenic soybean plant, the plant and its progeny carrying the introduced recombinant DNA in the same locus and chromosome are genetically identical for the transgenic event. A person of ordinary skill in the art of plant transformation understands that multiple transgenic events are required to achieve an event with a desired phenotype and without an off-type. For instance, recombinant DNA randomly inserted into a chromosome has the possibility of disrupting the function of a native gene to create an undesirable trait commonly called an "off-type". A selection method is designed to evaluate multiple transgenic plants (events) including the recombinant DNA sequence(s), for example multiple plants transformed with the DNA construct of the invention to produce from 2 to 20 or more, often hundreds, of transgenic events. This is to provide a population of transgenic plants that will allow selection of a transgenic plant exhibiting the target phenotype and without an off-type. For commercial purposes, a single insertion of an intact recombinant DNA construct is preferably in a single locus in a chromosome. Transgenic soybean plants produced from transgenic cells provided by this invention demonstrate improved agronomic traits (e. g., increased pods per node, increased number of internodes and nodes, decreased average internode length, or a twisted stem phenotype) as compared to a control plant that does not contain or express the recombinant DNA construct.

TABLE 5

| Function | Genetic Element | Description of Element |
| --- | --- | --- |
| *Agrobacterium* T-DNA transfer marker expression cassette | Atu left border | *Agrobacterium* left border for transfer of T-DNA. |
| | Promoter | Promoter from the *Arabidopsis* actin 7 gene |
| | 5' UTR | 5' UTR of *Arabidopsis* Act7 gene |
| | Intron | Intron from the *Arabidopsis* actin7 gene |
| | Transit Peptide | Chloroplast transit peptide region of *Arabidopsis* EPSPS |
| | Marker | Synthetic DNA with divot preferred codon usage for glyphosate resistant EPSPS. |
| | 3' UTR | A 3' non-translated region of the nopaline synthase gene of *Agrobacterium tumefaciens* Ti plasmid which functions to direct polyadenylation of the mRNA. |
| RNA molecule expression cassette | Promoter | Enhanced 35 S promoter from CaMV |
| | DNA | DNA that is transcribed to an RNA molecule of SEQ ID NO: 91 that hybridizes to a mature miR171 miRNA. |
| | DNA | DNA that is transcribed to an RNA molecule of SEQ ID NO: 119 that hybridizes to a in iR171 target gene. |
| | 3' UTR | 3' untranslated region from the fiber protein E6 gene of sea-island cotton. |

TABLE 5-continued

| Function | Genetic Element | Description of Element |
|---|---|---|
| Agrobacterium T-DNA transfer | Atu right border | Agrobacterium right border for transfer of T-DNA. |
| Maintenance in E. coli | OR-Ec.oriV-RK2 | The vegetative origin of replication from plasm id RK2. |
| | OR-Ec.ori-ColE1 | The minimal origin of replication from the E. coli plasmid ColE 1. |
| | Marker | Coding region for Tn7 adenylyltransferase (AAD(3")) conferring spectinomycin and streptomycin resistance. |
| | 3' UTR | 3' UTR from the Tn7 adenylyltransferase (AAD(3")) gene of E. coli. |
| | Promoter | Promoter for Tn7 adenylyltransferase (AAD(3")) |
| | CR-Ec.rop | Coding region for repressor of primer from the ColE1 plasmid. Expression of this gene product interferes with primer binding at the origin of replication, keeping plasmid copy number low. |

The seeds of transgenic soybean plants can be harvested from fertile transgenic plants and be used to grow progeny generations of transformed plants of this invention. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with recombinant DNA providing an enhanced trait, e. g., increased pods per node, can be crossed with a transgenic plant line having other recombinant DNA that confers another trait, for example herbicide resistance or pest resistance, to produce progeny plants having recombinant DNA that confers both traits. Genetic markers associated with recombinant DNA are useful for producing transgenic progeny that is homozygous for the desired recombinant DNA. Progeny plants carrying DNA for both parental traits can be back crossed into a parent line multiple times, for example usually 6 to 8 generations, to produce a progeny plant with substantially the same genotype as the one original transgenic parental line but having the recombinant DNA of the other transgenic parental line. The term "progeny" denotes the offspring of any generation of a parent plant prepared by the methods of this invention containing the recombinant DNA that produces an RNA molecule that hybridizes to a mature miR171 miRNA.

Example 1

Figure 2:
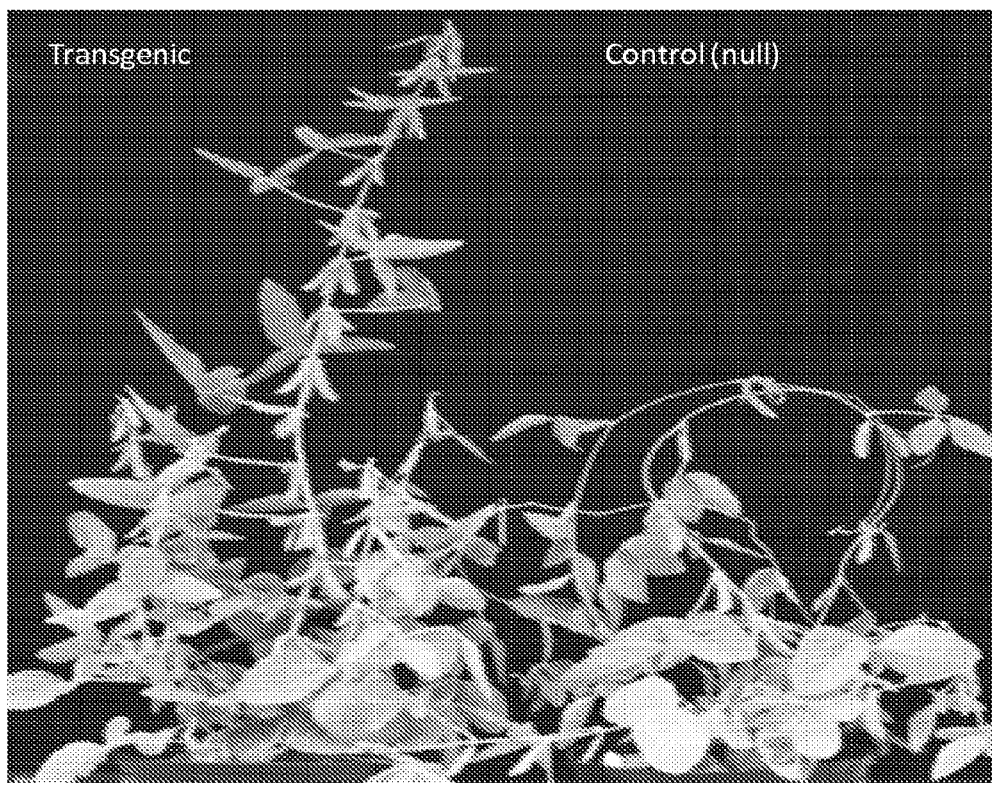
FIG. 2 is a photograph illustrating characteristics of a non-natural transgenic soybean plant having a chromosome of the invention relative to a control plant.
Figure 3A:
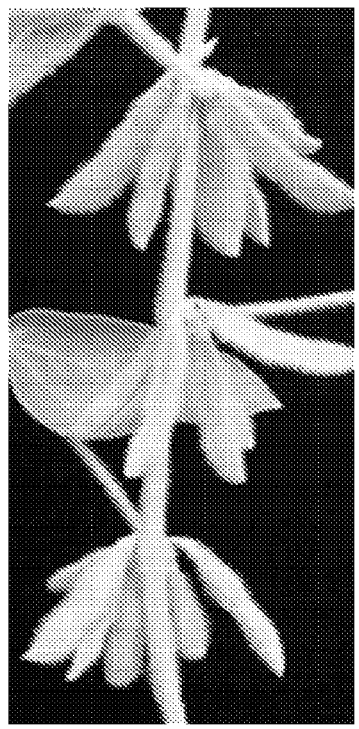
FIGS. 3A-3B are photographs illustrating characteristics of a non-natural transgenic soybean plant having a chromosome of the invention that imparts an increased pods per node phenotype (FIG. 3A) and a twisted stem phenotype (FIG. 3B).
Figure 3B:
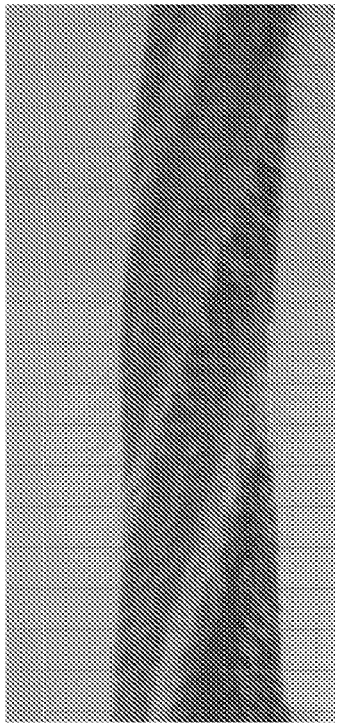
Figure 4:
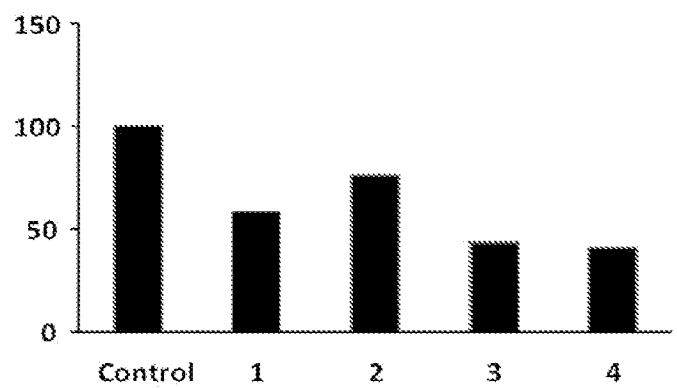
FIGS. 4A-4B graphically illustrates characteristics of a non-natural transgenic soybean plant having a chromosome of the invention that imparts a decreased internode length (FIG. 4A) and an increased pod number (FIG. 4B) compared to a non-transgenic control plant.
Figure 4:
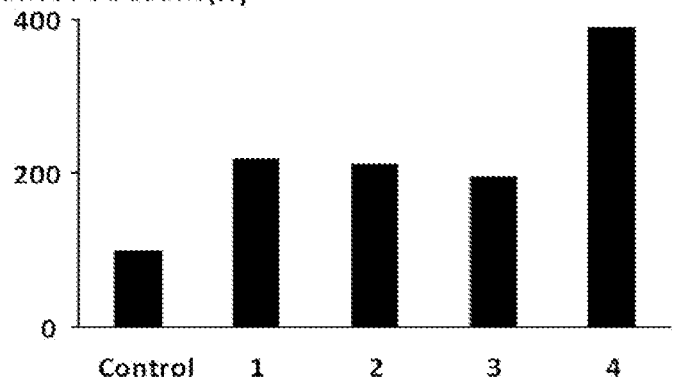

This example illustrates soybean transformation useful in producing transgenic soybean chromosomes, cells, plants and plant parts of this invention. A plasmid as shown in Table 5 is used in procedures disclosed in Patent Application Publication US2009/0138985A1 to transfer the recombinant DNA for transcribing an RNA molecule of this invention into a chromosome in a soybean cell. Multiple events of soybean cells with recombinant DNA located in different loci in a transgenic soybean chromosome are produced. Such non-natural transgenic soybean chromosomes include recombinant DNA that is transcribed to an RNA molecule that hybridizes under physiological conditions to a mature miR171 miRNA to form a cleavage-resistant duplex. Transgenic cells for each transgenic event are regenerated into transgenic plants. With reference to FIG. 2 transgenic soybean plants having the DNA construct that transcribes to an RNA molecules of SEQ ID NO: 93 exhibited high phenotypic penetrance and agronomic characteristics of increased pods per node, increased number of nodes and internodes, and a decreased distance between internodes, as compared to a control non-transgenic soybean plant. With reference to FIG. 3 there is shown in FIG. 3A, a transgenic soybean plant having 5-6 pods on each of 3 separate nodes; in FIG. 3B, there is shown the rigid stalk and twisted stem phenotype exhibited by the transgenic plant. Separate events of transgenic plants show a decrease in the internodal distance and increased pods per node per plant (FIG. 4). With reference to FIG. 4 there is shown the enhanced traits in soybean plants from 4 separate transformation events that have a reduction in internode length per plant (FIG. 4A) and an increase in relative pod count per plant (FIG. 4B), as compared to a non-transgenic control plant.

Example 2

This example illustrates further embodiments of the invention where multiple transgenic soybean chromosomes are prepared as described in Example 1 except that the DNA that is transcribed to an RNA molecule of SEQ ID NO: 93 that hybridizes to a mature miR171 miRNA is replaced in separate chromosomes by each of a DNA that is transcribed to one of the RNA molecules having an RNA nucleotide sequence of SEQ ID NOS: 94-118 that is designed to hybridize to and form a cleavage-resistant duplex with a mature mir171 miRNA. Multiple soybean transgenic events are produced for each separate recombinant DNA construct transformed into soybean cells which are regenerated into transgenic soybean plants having a chromosome of this invention. The transgenic soybean plants are grown to maturity and screened to identify at least one event having the appropriate recombinant DNA construct (one of SEQ ID NOS: 93-118) and that exhibits an enhanced phenotypic trait, e. g., an increased number of pods per node compared to a control plant.

Example 3

This example illustrates embodiments of the invention where a transgenic soybean chromosome is prepared as described in Example 1 except that the DNA that is transcribed to an RNA molecule of SEQ ID NO: 119 that hybridizes to a mature miR171 miRNA is replaced in separate chromosomes by each of a DNA that is transcribed to one of the RNA molecules having an RNA nucleotide sequence of SEQ ID NOS: 119-143 that is designed to hybridize to and form a cleavage-resistant duplex with a transcript of a target gene having a recognition site for a mature miR171 miRNA, i. e., a miR171 miRNA recognition site on the transcript of a miR171-regulated soybean gene. Multiple soybean transgenic events are produced for each separate recombinant DNA construct transformed into soybean cells which are regenerated into transgenic soybean plants having a chromosome of this invention. The transgenic soybean plants are grown to maturity and screened to identify at least one event having the appropriate recombinant DNA construct (one of SEQ ID NOS: 119-143) and that exhibits an enhanced phenotypic trait, e. g., an increased number of pods per node compared to a control plant.

Example 4

This example illustrates an aspect of the invention including dead transgenic soybean plants having increased pods per node, where the pods contain viable transgenic soybean seeds having the non-natural transgenic soybean chromosomes of this invention. The transgenic soybean plants produced in Examples 1, 2 and 3 are screened to identify transgenic soybean plants having a chromosome of this invention. Such plants are grown to maturity and exhibit increased pods as compared to a non-transgenic control soybean control plant. The mature soybean plants are allowed to senesce into dead, non-viable plants. The viable seed collected from the dead plants are screened to identify homozygous transgenic seeds which are replanted to produce homozygous transgenic plants exhibiting increased pods per node. A quantity of the transgenic seed is also processed into a meal which can be used as an industrial raw material.

Example 5

This example illustrates still another embodiment of the invention relating to the utility of dead soybean plants of this invention. Viable transgenic soybean seeds are harvested from the soybean plants of Example 4 when the dead, senesced, leafless, non-natural, transgenic plants are aged to the point where the soybean seeds are air dried in the mature bean pods to contain between 8 and 18 percent moisture. The harvested, viable, transgenic soybean seeds have a transgenic chromosome of this invention and are segregated into a population of seeds that are designated for planting and a population of seeds that are designated for crushing into a processed seed meal. Seeds that are designated for planting are saved for the next planting season and planted to produce transgenic soybean plants of this invention. Seeds that are designated for crushing are processed by milling to produce soybean meal having residual DNA in the form of chromosomes of this invention and to produce soybean oil that does not contain residual DNA and is processed into biodiesel fuel.

What is claimed is:

1. A soybean plant cell, wherein the cell comprises a recombinant DNA construct comprising DNA that is transcribed into an RNA molecule that, under physiological conditions in the soybean plant cell of a soybean plant growing at temperatures between about 20° C. to about 30° C. and at a relative humidity between about 50-100%, hybridizes to and forms a cleavage-resistant duplex with a mature miR171 miRNA, wherein the mature miR171 miRNA comprises a consensus RNA nucleotide sequence of SEQ ID NO:91 or SEQ ID NO:92 including a cleavage site, and wherein the RNA molecule has one or more nucleotide mismatches with the mature miR171 miRNA, whereby the function of said mature miR171 mRNA is inhibited in said soybean plant cell by the RNA molecule, and wherein said soybean plant cell is in a non-natural, transgenic soybean plant having enhanced agronomic characteristics selected from a group consisting of increased pods per node, increased number of internodes and nodes, decreased average internode length, and a twisted stem phenotype as compared to a control and further wherein the sequence of the RNA molecule has at least one nucleotide addition or deletion relative to a sequence complementary to SEQ ID NO:91 or 92.

2. The soybean plant cell of claim 1, wherein the cleavage-resistant duplex between the RNA molecule and the mature miR171 miRNA includes at least one mismatch at the cleavage site of the mature miR171 miRNA.

3. The soybean plant cell of claim 1, wherein the cleavage site of the mature miR171 miRNA is between nucleotides that correspond to the nucleotides at positions 10 and 11 of one of the consensus RNA nucleotide sequences of SEQ ID NO: 91 or SEQ ID NO: 92 that best aligns with the nucleotide RNA sequence of the mature miR171 miRNA, and wherein the RNA molecule is not perfectly base-paired with the mature miR171 miRNA either (a) at least at a nucleotide corresponding to positions 10 or 11 at the cleavage site of the mature miR171 miRNA, or (b) at least at nucleotide positions corresponding to positions 10 and 11 at the cleavage site of the mature miR171 miRNA.

4. The soybean plant cell of claim 1, wherein the RNA molecule includes at least three insertion nucleotides between the nucleotides of the RNA molecule that are complementary to positions 10 and 11 at the cleavage site of the mature miR171 miRNA.

5. The soybean plant cell of claim 1, wherein the RNA molecule is at least 11 nucleotides in length.

6. The soybean plant cell of claim 1, wherein said cleavage-resistant duplex is formed at least partially with the consensus sequence of the mature miR171 miRNA.

7. The soybean plant cell of claim 6, wherein said cleavage-resistant duplex comprises at least 6 base pairs in said consensus sequence.

8. The soybean plant cell of claim 1, wherein said cleavage-resistant duplex between said RNA molecule and said miR171 miRNA includes at least two mismatches at the cleavage site of said mature miR171 miRNA.

9. The soybean plant cell of claim 1, wherein said cleavage-resistant duplex comprises:

a. at least one mismatch between said RNA molecule and said mature miR171 miRNA at a nucleotide position of the mature miR171 miRNA corresponding to position 9, 10, 11 or 12 of SEQ ID NO:91 or SEQ ID NO:92, or b. at least one insertion at a position within said RNA molecule between nucleotides of the RNA molecule that are complementary to nucleotide positions of the mature miR171 corresponding to positions 10-12 of SEQ ID NO:91 or SEQ ID NO:92, or c. a mismatch at a position within the RNA molecule complementary to the 3' end of the consensus sequence of the mature miR171 miRNA corresponding to SEQ ID NO:91 or SEQ ID NO:92.

10. The soybean plant cell of claim 1, wherein the RNA molecule comprises a RNA nucleotide sequence selected from the group consisting of SEQ ID NO: 93 through SEQ ID NO: 118.

11. An industrial raw material including the soybean plant cell of claim 1.

12. The industrial raw material of claim 11, comprising crushed soybean seeds.

13. A non-natural transgenic soybean plant having a soybean plant cell of claim 1.

14. A non-natural transgenic soybean seed having a soybean plant cell of claim 1.

15. A dead non-natural transgenic soybean plant having mature bean pods containing non-natural, transgenic soybean seeds having the soybean plant cell of claim 1.

16. A method of increasing pods per node, number of internodes and nodes or a twisted stem in a soybean plant by providing in the soybean plant a soybean plant cell of claim 1.

17. The soybean plant cell of claim 1, wherein the sequence of the RNA molecule has an at least two nucleotide addition or deletion relative to a sequence complementary to SEQ ID NO:91 or 92.

18. The soybean plant cell of claim 1, wherein the RNA molecule has at least one insertion nucleotide, relative to corresponding sequence of the miR171 miRNA, between the nucleotides of the RNA molecule that are complementary to nucleotides at the cleavage site of the mature miR171 miRNA.

19. The soybean plant cell of claim 1, wherein the nucleotides at the cleavage site of the mature miR171 miRNA correspond to positions 10 and 11 of SEQ ID NOS: 91 or 92.

20. The soybean plant cell of claim 1, wherein the sequence of the RNA molecule has up to 2 nucleotide additions or up to 2 nucleotide deletions at the 5' terminus, the 3' terminus, or both the 3' and 5' termini, of a recognition site of the mature miR171 miRNA.

21. The soybean plant cell of claim 1, wherein the RNA molecule is between 19 and 26 nucleotides in length.

* * * * *

SEQUENCE LISTING

```
<160> NUMBER OF SEQ ID NOS: 143

<210> SEQ ID NO 1
<211> LENGTH: 123
<212> TYPE: RNA
<213> ORGANISM: Arabidopsis thaliana

<400> SEQUENCE: 1
augagagagu cccuuugaua uuggccuggu ucacucagau cuuaccugac cacacacgua      60
gauauacauu auucucucua gauuaucuga uugagccgcg ccaauaucuc aguacucucu     120
cgu                                                                  123

<210> SEQ ID NO 2
<211> LENGTH: 117
<212> TYPE: RNA
<213> ORGANISM: Arabidopsis thaliana

<400> SEQUENCE: 2
ugcaagguaa cgcgagauau uagugcgguu caaucaaaua gucguccucu uaacucaugg      60
agaacggugu uguucgauug agccgugcca auaucacgcg guaaaccaaa aauggca        117

<210> SEQ ID NO 3
<211> LENGTH: 100
<212> TYPE: RNA
<213> ORGANISM: Oryza sativa

<400> SEQUENCE: 3
gcgacgacgg gauauugggg cgguucaauc agaaagcuug ugcuccggaa gcgaggagcu      60
cuacucuuuu gauugagccg ugccaauauc acgucgcauc                           100

<210> SEQ ID NO 4
<211> LENGTH: 89
<212> TYPE: RNA
<213> ORGANISM: Oryza sativa

<400> SEQUENCE: 4
gacauggcau gguauugacu uggcucaucu cagcaacagc aaacugcaug cagcgcugga      60
ggugagccga gccaauauca cuucauguc                                       89

<210> SEQ ID NO 5
<211> LENGTH: 120
```

```
<212> TYPE: RNA
<213> ORGANISM: Oryza sativa

<400> SEQUENCE: 5
uaaaaagagg uauuggcgug ccucaauccg aaggcauggc ugauuacagg caccucgacc    60
gaucuagcgc augcagccau guuucuugga uugagccgcg ucaauaucuc uccuugcuuc   120

<210> SEQ ID NO 6
<211> LENGTH: 124
<212> TYPE: RNA
<213> ORGANISM: Sorghum bicolor

<400> SEQUENCE: 6
aggaggaaga agacgacaug gcgugguauu guuucggcuc auguccuucu ugcuucgagu    60
cugucgucgg auuuuggaug ugaugugagc cgaaccaaua ucacucaugu auucuucauu   120
cuga                                                                124

<210> SEQ ID NO 7
<211> LENGTH: 119
<212> TYPE: RNA
<213> ORGANISM: Sorghum bicolor

<400> SEQUENCE: 7
ugagagaaua agacgacaug gcgugauguu guuucggcuc augcauaucc uucuugagug    60
uaucaucagg aaagaggcga ugagccgaac caauaucacu cauguauucu ucauucaua   119

<210> SEQ ID NO 8
<211> LENGTH: 114
<212> TYPE: RNA
<213> ORGANISM: Medicago truncatula

<400> SEQUENCE: 8
ugaauucccc uccgcuuuuu gauguuggcu ugcucaauc aaaucaaagu ucuugaaauu    60
ugaguucuuu agucugauug agucgugcca auaucauauu aagcgauaaa aguc         114

<210> SEQ ID NO 9
<211> LENGTH: 85
<212> TYPE: RNA
<213> ORGANISM: Zea mays

<400> SEQUENCE: 9
cgggauauug gcgcgguuca aucagaaagc uugcgcucca ggcccgaggg gcuccacucu    60
uugauugagc cgugccaaua ucacg                                         85

<210> SEQ ID NO 10
<211> LENGTH: 118
<212> TYPE: RNA
<213> ORGANISM: Zea mays

<400> SEQUENCE: 10
ggggaaucga aaccuacgg gauauuggug cgguucaauc agaaagcuug cgcuccaaag    60
cccaggggcu ccacucuuug acugagccgu gccaauauca cguccucgcu uugcuugc    118

<210> SEQ ID NO 11
<211> LENGTH: 155
<212> TYPE: RNA
<213> ORGANISM: Zea mays

<400> SEQUENCE: 11
```

```
uugguuguug gcugagagag ugcgauguug gcauggcuca aucaacucgc cggccgcggg    60
uggcuuauag cuuaauucug cgcauucgau cgaggugcgg gcgcaguguu uaauugauug   120
agccgugcca auaucacaac cuucucuagc cuaua                              155

<210> SEQ ID NO 12
<211> LENGTH: 104
<212> TYPE: RNA
<213> ORGANISM: Brassica napus

<400> SEQUENCE: 12
uggucaagcg agauauuagu gcgguucaau caaauagucu cacucuuagu ugauagagau    60
ugauuuuguu cgauugagcc gugccaauau cacgcauaua acca                   104

<210> SEQ ID NO 13
<211> LENGTH: 101
<212> TYPE: RNA
<213> ORGANISM: Brassica napus

<400> SEQUENCE: 13
gguaacgcga gauauuagug cgguucaauc aaauagucgu guucucacuu gauagagauc    60
gguuuuguuc gauugagccg ugccaauauc acgcgucaac c                      101

<210> SEQ ID NO 14
<211> LENGTH: 88
<212> TYPE: RNA
<213> ORGANISM: Brassica napus

<400> SEQUENCE: 14
gcgagauauu agugcgguuc aaucaaauag ucguacucuu agcuauuaga gaucgguuuu    60
guucgauuga gccgugccaa uaucacgc                                      88

<210> SEQ ID NO 15
<211> LENGTH: 80
<212> TYPE: RNA
<213> ORGANISM: Brassica napus

<400> SEQUENCE: 15
gauauuggcc ugguucacuc agauuacaca cguacuauau gcauucucuu aguuaucuga    60
uugagccgcg ccaauaucuc                                               80

<210> SEQ ID NO 16
<211> LENGTH: 130
<212> TYPE: RNA
<213> ORGANISM: Triticum aestivum

<400> SEQUENCE: 16
uggaaugguc acuaugaugu uggcucgacu cacucagacc acgccugccg gccggccgua    60
gccaugcauc ugcaugcggu ggugcucug auugagccgu gccaauaucu cagugcucuu   120
ucaugcaugc                                                          130

<210> SEQ ID NO 17
<211> LENGTH: 21
<212> TYPE: RNA
<213> ORGANISM: Arabidopsis thaliana

<400> SEQUENCE: 17
ugauugagcc gcgccaauau c                                             21
```

```
<210> SEQ ID NO 18
<211> LENGTH: 21
<212> TYPE: RNA
<213> ORGANISM: Arabidopsis thaliana

<400> SEQUENCE: 18
uugagccgug ccaauaucac g                                              21

<210> SEQ ID NO 19
<211> LENGTH: 21
<212> TYPE: RNA
<213> ORGANISM: Oryza sativa

<400> SEQUENCE: 19
ugauugagcc gugccaauau c                                              21

<210> SEQ ID NO 20
<211> LENGTH: 21
<212> TYPE: RNA
<213> ORGANISM: Oryza sativa

<400> SEQUENCE: 20
gaggugagcc gagccaauau c                                              21

<210> SEQ ID NO 21
<211> LENGTH: 21
<212> TYPE: RNA
<213> ORGANISM: Oryza sativa

<400> SEQUENCE: 21
ggauugagcc gcgucaauau c                                              21

<210> SEQ ID NO 22
<211> LENGTH: 21
<212> TYPE: RNA
<213> ORGANISM: Sorghum bicolor

<400> SEQUENCE: 22
gugagccgaa ccaauaucac u                                              21

<210> SEQ ID NO 23
<211> LENGTH: 21
<212> TYPE: RNA
<213> ORGANISM: Sorghum bicolor

<400> SEQUENCE: 23
ugagccgugc caauaucacg a                                              21

<210> SEQ ID NO 24
<211> LENGTH: 21
<212> TYPE: RNA
<213> ORGANISM: Medicago truncatula

<400> SEQUENCE: 24
ugauugaguc gugccaauau c                                              21

<210> SEQ ID NO 25
<211> LENGTH: 20
<212> TYPE: RNA
<213> ORGANISM: Zea mays

<400> SEQUENCE: 25
uugagccgug ccaauaucac                                                20
```

```
<210> SEQ ID NO 26
<211> LENGTH: 21
<212> TYPE: RNA
<213> ORGANISM: Zea mays

<400> SEQUENCE: 26
ugacugagcc gugccaauau c                                              21

<210> SEQ ID NO 27
<211> LENGTH: 21
<212> TYPE: RNA
<213> ORGANISM: Zea mays

<400> SEQUENCE: 27
uugagccgug ccaauaucac a                                              21

<210> SEQ ID NO 28
<211> LENGTH: 21
<212> TYPE: RNA
<213> ORGANISM: Brassica napus

<400> SEQUENCE: 28
uugagccgug ccaauaucac g                                              21

<210> SEQ ID NO 29
<211> LENGTH: 21
<212> TYPE: RNA
<213> ORGANISM: Brassica napus

<400> SEQUENCE: 29
uauuggugcg guucaaugag a                                              21

<210> SEQ ID NO 30
<211> LENGTH: 20
<212> TYPE: RNA
<213> ORGANISM: Brassica napus

<400> SEQUENCE: 30
uugagccgcg ccaauaucac                                                20

<210> SEQ ID NO 31
<211> LENGTH: 21
<212> TYPE: RNA
<213> ORGANISM: Brassica napus

<400> SEQUENCE: 31
cgagccgaau caauaucacu c                                              21

<210> SEQ ID NO 32
<211> LENGTH: 21
<212> TYPE: RNA
<213> ORGANISM: Triticum aestivum

<400> SEQUENCE: 32
ugauugagcc gugccaauau c                                              21

<210> SEQ ID NO 33
<211> LENGTH: 21
<212> TYPE: RNA
<213> ORGANISM: Arabidopsis thaliana

<400> SEQUENCE: 33
ugauugagcc gggccaauau c                                              21
```

<210> SEQ ID NO 34
<211> LENGTH: 24
<212> TYPE: RNA
<213> ORGANISM: Arabidopsis thaliana

<400> SEQUENCE: 34
cauugagccg ugccaauauc acgc                                          24

<210> SEQ ID NO 35
<211> LENGTH: 19
<212> TYPE: RNA
<213> ORGANISM: Arabidopsis thaliana

<400> SEQUENCE: 35
auugagccgu gucaauauc                                                19

<210> SEQ ID NO 36
<211> LENGTH: 21
<212> TYPE: RNA
<213> ORGANISM: Arabidopsis thaliana

<400> SEQUENCE: 36
ugauugagcc gugucaauau c                                             21

<210> SEQ ID NO 37
<211> LENGTH: 21
<212> TYPE: RNA
<213> ORGANISM: Arabidopsis thaliana

<400> SEQUENCE: 37
ugauugagcc gugacaauau c                                             21

<210> SEQ ID NO 38
<211> LENGTH: 20
<212> TYPE: RNA
<213> ORGANISM: Zea mays

<400> SEQUENCE: 38
ugauugagcc gcgccaauau                                               20

<210> SEQ ID NO 39
<211> LENGTH: 21
<212> TYPE: RNA
<213> ORGANISM: Zea mays

<400> SEQUENCE: 39
ugacugagcc gugccaauau c                                             21

<210> SEQ ID NO 40
<211> LENGTH: 21
<212> TYPE: RNA
<213> ORGANISM: Oryza sativa

<400> SEQUENCE: 40
ugauugagcc gugccgauau c                                             21

<210> SEQ ID NO 41
<211> LENGTH: 19
<212> TYPE: RNA
<213> ORGANISM: Oryza sativa

<400> SEQUENCE: 41
auugagccgu gccaauauc 19

<210> SEQ ID NO 42
<211> LENGTH: 21
<212> TYPE: RNA
<213> ORGANISM: Oryza sativa

<400> SEQUENCE: 42
ugauuuagcc gugccaauau c 21

<210> SEQ ID NO 43
<211> LENGTH: 19
<212> TYPE: RNA
<213> ORGANISM: Oryza sativa

<400> SEQUENCE: 43
ugauugagcc gugccaaua 19

<210> SEQ ID NO 44
<211> LENGTH: 21
<212> TYPE: RNA
<213> ORGANISM: Oryza sativa

<400> SEQUENCE: 44
ugauugaacc gugccaauau c 21

<210> SEQ ID NO 45
<211> LENGTH: 21
<212> TYPE: RNA
<213> ORGANISM: Oryza sativa

<400> SEQUENCE: 45
ugauuaagcc gugccaauau c 21

<210> SEQ ID NO 46
<211> LENGTH: 23
<212> TYPE: RNA
<213> ORGANISM: Oryza sativa

<400> SEQUENCE: 46
ugauugagcc guugccaaua uuc 23

<210> SEQ ID NO 47
<211> LENGTH: 21
<212> TYPE: RNA
<213> ORGANISM: Oryza sativa

<400> SEQUENCE: 47
ugauugaccc gugccaauau c 21

<210> SEQ ID NO 48
<211> LENGTH: 21
<212> TYPE: RNA
<213> ORGANISM: Oryza sativa

<400> SEQUENCE: 48
ugauugagcc guuccaauau c 21

<210> SEQ ID NO 49
<211> LENGTH: 21
<212> TYPE: RNA
<213> ORGANISM: Oryza sativa

<400> SEQUENCE: 49

-continued ugauugagac gugccaauau c          21

<210> SEQ ID NO 50
<211> LENGTH: 21
<212> TYPE: RNA
<213> ORGANISM: Oryza sativa

<400> SEQUENCE: 50
ugauugagcc gugccaauac c          21

<210> SEQ ID NO 51
<211> LENGTH: 21
<212> TYPE: RNA
<213> ORGANISM: Oryza sativa

<400> SEQUENCE: 51
ugauugagcc gugcaaauau c          21

<210> SEQ ID NO 52
<211> LENGTH: 21
<212> TYPE: RNA
<213> ORGANISM: Oryza sativa

<400> SEQUENCE: 52
ugauucagcc gugccaauau c          21

<210> SEQ ID NO 53
<211> LENGTH: 21
<212> TYPE: RNA
<213> ORGANISM: Oryza sativa

<400> SEQUENCE: 53
ugauugagcc gucccaauau c          21

<210> SEQ ID NO 54
<211> LENGTH: 21
<212> TYPE: RNA
<213> ORGANISM: Oryza sativa

<400> SEQUENCE: 54
ugauugagcc gugcuaauau c          21

<210> SEQ ID NO 55
<211> LENGTH: 21
<212> TYPE: RNA
<213> ORGANISM: Oryza sativa

<400> SEQUENCE: 55
ugauugagca gugccaauau c          21

<210> SEQ ID NO 56
<211> LENGTH: 21
<212> TYPE: RNA
<213> ORGANISM: Oryza sativa

<400> SEQUENCE: 56
ugauugaucc gugccaauau c          21

<210> SEQ ID NO 57
<211> LENGTH: 21
<212> TYPE: RNA
<213> ORGANISM: Oryza sativa

```
<400> SEQUENCE: 57
ugauagagcc gugccaauau c                                              21

<210> SEQ ID NO 58
<211> LENGTH: 21
<212> TYPE: RNA
<213> ORGANISM: Oryza sativa

<400> SEQUENCE: 58
ugauugagcc gugccuauau c                                              21

<210> SEQ ID NO 59
<211> LENGTH: 21
<212> TYPE: RNA
<213> ORGANISM: Oryza sativa

<400> SEQUENCE: 59
ugauugagcu gugccaauau c                                              21

<210> SEQ ID NO 60
<211> LENGTH: 21
<212> TYPE: RNA
<213> ORGANISM: Oryza sativa

<400> SEQUENCE: 60
ugauugagcc gugccaauau a                                              21

<210> SEQ ID NO 61
<211> LENGTH: 21
<212> TYPE: RNA
<213> ORGANISM: Oryza sativa

<400> SEQUENCE: 61
ugauugagcc gugccaguau c                                              21

<210> SEQ ID NO 62
<211> LENGTH: 21
<212> TYPE: RNA
<213> ORGANISM: Oryza sativa

<400> SEQUENCE: 62
ugauugagcc gugcccauau c                                              21

<210> SEQ ID NO 63
<211> LENGTH: 24
<212> TYPE: RNA
<213> ORGANISM: Oryza sativa

<400> SEQUENCE: 63
ugauugagcc gugccaauau cugg                                           24

<210> SEQ ID NO 64
<211> LENGTH: 21
<212> TYPE: RNA
<213> ORGANISM: Oryza sativa

<400> SEQUENCE: 64
cgauugagcc gugccaauau c                                              21

<210> SEQ ID NO 65
<211> LENGTH: 21
<212> TYPE: RNA
<213> ORGANISM: Oryza sativa
```

-continued

```
<400> SEQUENCE: 65
uuauugagcc gugccaauau c                                      21

<210> SEQ ID NO 66
<211> LENGTH: 19
<212> TYPE: RNA
<213> ORGANISM: Oryza sativa

<400> SEQUENCE: 66
ugauugagcc gugccgaua                                         19

<210> SEQ ID NO 67
<211> LENGTH: 21
<212> TYPE: RNA
<213> ORGANISM: Oryza sativa

<400> SEQUENCE: 67
ugauugagcc gugccaauau u                                      21

<210> SEQ ID NO 68
<211> LENGTH: 21
<212> TYPE: RNA
<213> ORGANISM: Oryza sativa

<400> SEQUENCE: 68
cauugagccg ugccaauauc a                                      21

<210> SEQ ID NO 69
<211> LENGTH: 22
<212> TYPE: RNA
<213> ORGANISM: Oryza sativa

<400> SEQUENCE: 69
ugauugagcc gugccaauau cc                                     22

<210> SEQ ID NO 70
<211> LENGTH: 21
<212> TYPE: RNA
<213> ORGANISM: Oryza sativa

<400> SEQUENCE: 70
ugauugagcc gugccacuau c                                      21

<210> SEQ ID NO 71
<211> LENGTH: 24
<212> TYPE: RNA
<213> ORGANISM: Oryza sativa

<400> SEQUENCE: 71
aucugauuga gccgugccaa uauc                                   24

<210> SEQ ID NO 72
<211> LENGTH: 22
<212> TYPE: RNA
<213> ORGANISM: Oryza sativa

<400> SEQUENCE: 72
uugauugagc cgugccaaua uc                                     22

<210> SEQ ID NO 73
<211> LENGTH: 23
<212> TYPE: RNA
```

```
<213> ORGANISM: Oryza sativa

<400> SEQUENCE: 73
ucugauugag ccgugccaau auc                                          23

<210> SEQ ID NO 74
<211> LENGTH: 22
<212> TYPE: RNA
<213> ORGANISM: Oryza sativa

<400> SEQUENCE: 74
cugauugagc cgugccaaua uc                                           22

<210> SEQ ID NO 75
<211> LENGTH: 21
<212> TYPE: RNA
<213> ORGANISM: Oryza sativa

<400> SEQUENCE: 75
ugauugagcc gugccaaucu c                                            21

<210> SEQ ID NO 76
<211> LENGTH: 23
<212> TYPE: RNA
<213> ORGANISM: Oryza sativa

<400> SEQUENCE: 76
ugauugagcc gugccaauau uuu                                          23

<210> SEQ ID NO 77
<211> LENGTH: 21
<212> TYPE: RNA
<213> ORGANISM: Oryza sativa

<400> SEQUENCE: 77
ugauugagcc gugccaauuu c                                            21

<210> SEQ ID NO 78
<211> LENGTH: 21
<212> TYPE: RNA
<213> ORGANISM: Oryza sativa

<400> SEQUENCE: 78
ugcuugagcc gugccaauau c                                            21

<210> SEQ ID NO 79
<211> LENGTH: 21
<212> TYPE: RNA
<213> ORGANISM: Medicago truncatula

<400> SEQUENCE: 79
ugauugaguc gugccaauau c                                            21

<210> SEQ ID NO 80
<211> LENGTH: 21
<212> TYPE: RNA
<213> ORGANISM: Medicago truncatula

<400> SEQUENCE: 80
ugauugaguc gugucaauau c                                            21

<210> SEQ ID NO 81
<211> LENGTH: 22
```

-continued

<212> TYPE: RNA
<213> ORGANISM: Brassica napus

<400> SEQUENCE: 81
ugauugagcc gcgccaauau cu                                        22

<210> SEQ ID NO 82
<211> LENGTH: 22
<212> TYPE: RNA
<213> ORGANISM: Brassica napus

<400> SEQUENCE: 82
ugauugagcc gugccaauau uu                                        22

<210> SEQ ID NO 83
<211> LENGTH: 22
<212> TYPE: RNA
<213> ORGANISM: Brassica napus

<400> SEQUENCE: 83
ugauugagcc gugccaauau cu                                        22

<210> SEQ ID NO 84
<211> LENGTH: 21
<212> TYPE: RNA
<213> ORGANISM: Vitris vinifera

<400> SEQUENCE: 84
uuugauugag ccgcgucaau a                                         21

<210> SEQ ID NO 85
<211> LENGTH: 19
<212> TYPE: RNA
<213> ORGANISM: Vitris vinifera

<400> SEQUENCE: 85
auugagccgc gucaauauc                                            19

<210> SEQ ID NO 86
<211> LENGTH: 21
<212> TYPE: RNA
<213> ORGANISM: Populus trichocarpa

<400> SEQUENCE: 86
ugagccgcgc caauaucaca u                                         21

<210> SEQ ID NO 87
<211> LENGTH: 21
<212> TYPE: RNA
<213> ORGANISM: Populus trichocarpa

<400> SEQUENCE: 87
agauugagcc gcgccaauau c                                         21

<210> SEQ ID NO 88
<211> LENGTH: 22
<212> TYPE: RNA
<213> ORGANISM: Populus trichocarpa

<400> SEQUENCE: 88
uagauugagc cgugccaaua uc                                        22

<210> SEQ ID NO 89

```
<211> LENGTH: 21
<212> TYPE: RNA
<213> ORGANISM: Populus trichocarpa

<400> SEQUENCE: 89
ggauugagcc gcgccaauau c                                              21

<210> SEQ ID NO 90
<211> LENGTH: 21
<212> TYPE: RNA
<213> ORGANISM: Salaginella moellendorffii

<400> SEQUENCE: 90
uugagccgug ccaauaucac u                                              21

<210> SEQ ID NO 91
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 91
ugauugagcc gcgccaauau c                                              21

<210> SEQ ID NO 92
<211> LENGTH: 21
<212> TYPE: RNA
<213> ORGANISM: artificial sequence
<220> FEATURE:
<223> OTHER INFORMATION: decoy and cleavage blocker for glycine max
      mir171
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u

<400> SEQUENCE: 92
uugagccgng ccaauaucac n                                              21

<210> SEQ ID NO 93
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 93
gauauuggcg cauaggcuca auca                                           24

<210> SEQ ID NO 94
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 94
gauauuggcg ucgcucaauc a                                              21
```

```
<210> SEQ ID NO 95
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 95
aauauuggug ucaaagcuca auca                                              24

<210> SEQ ID NO 96
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 96
ggugauauug cuacacggc ucaa                                               24

<210> SEQ ID NO 97
<211> LENGTH: 25
<212> TYPE: RNA
<213> ORGANISM: artificial sequence
<220> FEATURE:
<223> OTHER INFORMATION: decoy and cleavage blocker for glycine max
      mir171

<400> SEQUENCE: 97
aaauauuggu gucaaagcuc aauca                                             25

<210> SEQ ID NO 98
<211> LENGTH: 25
<212> TYPE: RNA
<213> ORGANISM: artificial sequence
<220> FEATURE:
<223> OTHER INFORMATION: decoy and cleavage blocker for glycine max
      mir171

<400> SEQUENCE: 98
agauuuuugu gugcaggcuc aauca                                             25

<210> SEQ ID NO 99
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 99
uuuguuggca caagugcuca auca                                              24

<210> SEQ ID NO 100
<211> LENGTH: 25
<212> TYPE: RNA
<213> ORGANISM: artificial sequence
<220> FEATURE:
<223> OTHER INFORMATION: decoy and cleavage blocker for glycine max
      mir171

<400> SEQUENCE: 100
gauauuggcg caauaggcuc aauca                                             25

<210> SEQ ID NO 101
```

-continued

```
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 101
gauauugacg uggcucaauc a                                            21

<210> SEQ ID NO 102
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 102
gauauuagug uggcucaauc a                                            21

<210> SEQ ID NO 103
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 103
gggcuuggcu uucuggcuca ccuc                                         24

<210> SEQ ID NO 104
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 104
gauaauuguu augcucaccu c                                            21

<210> SEQ ID NO 105
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 105
cguaguggcu gggcucaccu c                                            21

<210> SEQ ID NO 106
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 106
gauguugaca caccggcuca aucc                                         24

<210> SEQ ID NO 107
<211> LENGTH: 24
```

```
<212> TYPE: RNA
<213> ORGANISM: artificial sequence
<220> FEATURE:
<223> OTHER INFORMATION: decoy and cleavage blocker for glycine max
      mir171

<400> SEQUENCE: 107
gauauagcug ugccugcuca aucc                                              24

<210> SEQ ID NO 108
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 108
gauguuggca cuccugcuca aucc                                              24

<210> SEQ ID NO 109
<211> LENGTH: 23
<212> TYPE: RNA
<213> ORGANISM: artificial sequence
<220> FEATURE:
<223> OTHER INFORMATION: decoy and cleavage blocker for glycine max
      mir171

<400> SEQUENCE: 109
auauuggugu caaagcucaa uca                                               23

<210> SEQ ID NO 110
<211> LENGTH: 23
<212> TYPE: RNA
<213> ORGANISM: artificial sequence
<220> FEATURE:
<223> OTHER INFORMATION: decoy and cleavage blocker for glycine max
      mir171

<400> SEQUENCE: 110
gugauauugg cuacacggcu caa                                               23

<210> SEQ ID NO 111
<211> LENGTH: 23
<212> TYPE: RNA
<213> ORGANISM: artificial sequence
<220> FEATURE:
<223> OTHER INFORMATION: decoy and cleavage blocker for glycine max
      mir171

<400> SEQUENCE: 111
gaaguauugg ccagacggcu caa                                               23

<210> SEQ ID NO 112
<211> LENGTH: 23
<212> TYPE: RNA
<213> ORGANISM: artificial sequence
<220> FEATURE:
<223> OTHER INFORMATION: decoy and cleavage blocker for glycine max
      mir171

<400> SEQUENCE: 112
uugagguugg gcucgcggcu caa                                               23

<210> SEQ ID NO 113
<211> LENGTH: 24
<212> TYPE: RNA
```

```
<213> ORGANISM: artificial sequence
<220> FEATURE:
<223> OTHER INFORMATION: decoy and cleavage blocker for glycine max
      mir171

<400> SEQUENCE: 113
gaaauuugua cauaggcuca guca                                          24

<210> SEQ ID NO 114
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 114
ggugauauug gcuacacggc ucaa                                          24

<210> SEQ ID NO 115
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 115
gauguuguca cgcacacuca auca                                          24

<210> SEQ ID NO 116
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 116
guguguuuuu gggcgcgcgg cuca                                          24

<210> SEQ ID NO 117
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 117
gguguugccg ccgcggcuca aucu                                          24

<210> SEQ ID NO 118
<211> LENGTH: 24
<212> TYPE: RNA
<213> ORGANISM: artificial sequence
<220> FEATURE:
<223> OTHER INFORMATION: decoy and cleavage blocker for glycine max
      mir171

<400> SEQUENCE: 118
uauguuugcg uaugggcuca aucc                                          24

<210> SEQ ID NO 119
<211> LENGTH: 21
<212> TYPE: RNA
<213> ORGANISM: artificial sequence
```

```
<220> FEATURE:
<223> OTHER INFORMATION: decoy and cleavage blocker for glycine max
      mir171

<400> SEQUENCE: 119
ugauugagcc cggccaauau c                                              21

<210> SEQ ID NO 120
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 120
ugauugagcc gcgccaauau g                                              21

<210> SEQ ID NO 121
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 121
ugauugaggc gcgccaauau c                                              21

<210> SEQ ID NO 122
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 122
ugauugagcg gcgccaauau c                                              21

<210> SEQ ID NO 123
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 123
ugauugagcc ccgccaauau c                                              21

<210> SEQ ID NO 124
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 124
ugauugagcc gggccaauau c                                              21

<210> SEQ ID NO 125
<211> LENGTH: 21
<212> TYPE: RNA
<213> ORGANISM: artificial sequence
<220> FEATURE:
```

```
<223> OTHER INFORMATION: decoy and cleavage blocker for glycine max
      mir171

<400> SEQUENCE: 125
ugauugaggg gcgccaauau c                                            21

<210> SEQ ID NO 126
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 126
ugauugagcc gcgccaauau c                                            21

<210> SEQ ID NO 127
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 127
ugauugagcc gcgccaauau c                                            21

<210> SEQ ID NO 128
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 128
ugauugaggg ccgccaauau c                                            21

<210> SEQ ID NO 129
<211> LENGTH: 21
<212> TYPE: RNA
<213> ORGANISM: artificial sequence
<220> FEATURE:
<223> OTHER INFORMATION: decoy and cleavage blocker for glycine max
      mir171

<400> SEQUENCE: 129
ugauugaggg cggccaauau c                                            21

<210> SEQ ID NO 130
<211> LENGTH: 20
<212> TYPE: RNA
<213> ORGANISM: artificial sequence
<220> FEATURE:
<223> OTHER INFORMATION: decoy and cleavage blocker for glycine max
      mir171

<400> SEQUENCE: 130
ugauugagcg cgccaauauc                                              20

<210> SEQ ID NO 131
<211> LENGTH: 21
<212> TYPE: RNA
<213> ORGANISM: artificial sequence
<220> FEATURE:
<223> OTHER INFORMATION: decoy and cleavage blocker for glycine max
```

-continued mir171

<400> SEQUENCE: 131
ugauugagcc gcgccaauau c                                              21

<210> SEQ ID NO 132
<211> LENGTH: 20
<212> TYPE: RNA
<213> ORGANISM: artificial sequence
<220> FEATURE:
<223> OTHER INFORMATION: decoy and cleavage blocker for glycine max
      mir171

<400> SEQUENCE: 132
ugauugagcg cgccaauauc                                                20

<210> SEQ ID NO 133
<211> LENGTH: 20
<212> TYPE: RNA
<213> ORGANISM: artificial sequence
<220> FEATURE:
<223> OTHER INFORMATION: decoy and cleavage blocker for glycine max
      mir171

<400> SEQUENCE: 133
ugauugagcc cgccaauauc                                                20

<210> SEQ ID NO 134
<211> LENGTH: 20
<212> TYPE: RNA
<213> ORGANISM: artificial sequence
<220> FEATURE:
<223> OTHER INFORMATION: decoy and cleavage blocker for glycine max
      mir171

<400> SEQUENCE: 134
ugauugagcc ggccaauauc                                                20

<210> SEQ ID NO 135
<211> LENGTH: 19
<212> TYPE: RNA
<213> ORGANISM: artificial sequence
<220> FEATURE:
<223> OTHER INFORMATION: decoy and cleavage blocker for glycine max
      mir171

<400> SEQUENCE: 135
ugauugaggc gccaauauc                                                 19

<210> SEQ ID NO 136
<211> LENGTH: 19
<212> TYPE: RNA
<213> ORGANISM: artificial sequence
<220> FEATURE:
<223> OTHER INFORMATION: decoy and cleavage blocker for glycine max
      mir171

<400> SEQUENCE: 136
ugauugagcc gccaauauc                                                 19

<210> SEQ ID NO 137
<211> LENGTH: 19
<212> TYPE: RNA
<213> ORGANISM: artificial sequence
<220> FEATURE:
<223> OTHER INFORMATION: decoy and cleavage blocker for glycine max
      mir171

```
<400> SEQUENCE: 137
ugauugagcc gccaauauc                                                    19

<210> SEQ ID NO 138
<211> LENGTH: 18
<212> TYPE: RNA
<213> ORGANISM: artificial sequence
<220> FEATURE:
<223> OTHER INFORMATION: decoy and cleavage blocker for glycine max
      mir171

<400> SEQUENCE: 138
ugauugagcg ccaauauc                                                     18

<210> SEQ ID NO 139
<211> LENGTH: 18
<212> TYPE: RNA
<213> ORGANISM: artificial sequence
<220> FEATURE:
<223> OTHER INFORMATION: decoy and cleavage blocker for glycine max
      mir171

<400> SEQUENCE: 139
ugauugagcg ccaauauc                                                     18

<210> SEQ ID NO 140
<211> LENGTH: 17
<212> TYPE: RNA
<213> ORGANISM: artificial sequence
<220> FEATURE:
<223> OTHER INFORMATION: decoy and cleavage blocker for glycine max
      mir171

<400> SEQUENCE: 140
ugauugaggc caauauc                                                      17

<210> SEQ ID NO 141
<211> LENGTH: 16
<212> TYPE: RNA
<213> ORGANISM: artificial sequence
<220> FEATURE:
<223> OTHER INFORMATION: decoy and cleavage blocker for glycine max
      mir171

<400> SEQUENCE: 141
gagcccggcc aauaug                                                       16

<210> SEQ ID NO 142
<211> LENGTH: 17
<212> TYPE: RNA
<213> ORGANISM: artificial sequence
<220> FEATURE:
<223> OTHER INFORMATION: decoy and cleavage blocker for glycine max
      mir171

<400> SEQUENCE: 142
ugauugagcc cggccaa                                                      17

<210> SEQ ID NO 143
<211> LENGTH: 14
<212> TYPE: RNA
<213> ORGANISM: artificial sequence
<220> FEATURE:
<223> OTHER INFORMATION: decoy and cleavage blocker for glycine max
      mir171
<220> FEATURE:
```

```
<221> NAME/KEY: misc_feature
<222> LOCATION: (1)..(4)
<223> OTHER INFORMATION: n is a, c, g, or u

<400> SEQUENCE: 143
nnnnugauug agcc                                                    14
```